(12) United States Patent
Loushin et al.

(10) Patent No.: US 8,574,240 B2
(45) Date of Patent: Nov. 5, 2013

(54) STABILIZATION SYSTEM AND ASPIRATION DEVICE WITH PROTECTED CUTTING EDGE

(75) Inventors: Michael K. H. Loushin, Shoreview, MN (US); Keith J. Leland, Medina, MN (US)

(73) Assignee: Preceptis Medical, Inc., Shoreview, MN (US)

(*) Notice: Subject to any disclaimer, the term of this patent is extended or adjusted under 35 U.S.C. 154(b) by 16 days.

(21) Appl. No.: 13/346,245

(22) Filed: Jan. 9, 2012

(65) Prior Publication Data

US 2012/0179187 A1    Jul. 12, 2012

Related U.S. Application Data

(60) Provisional application No. 61/430,758, filed on Jan. 7, 2011.

(51) Int. Cl.
*A61F 11/00*    (2006.01)

(52) U.S. Cl.
USPC ........................................................ 606/109

(58) Field of Classification Search
USPC ..................... 606/108, 109, 167, 170, 185
See application file for complete search history.

(56) References Cited

U.S. PATENT DOCUMENTS

| | | | |
|---|---|---|---|
| 3,530,860 A | 9/1970 | Majoros | |
| 3,662,754 A | 5/1972 | Halloran | |
| 3,807,409 A | 4/1974 | Paparella et al. | |
| 3,871,380 A | 3/1975 | Heros | |
| 3,888,258 A | 6/1975 | Akiyama | |
| 3,897,786 A | 8/1975 | Garnett et al. | |
| 3,913,584 A | 10/1975 | Walchle et al. | |
| 3,948,271 A | 4/1976 | Akiyama | |
| 4,174,716 A | 11/1979 | Treace | |
| 4,334,538 A * | 6/1982 | Juhn | 604/35 |
| 4,445,517 A * | 5/1984 | Feild | 600/565 |
| 4,468,218 A | 8/1984 | Armstrong | |

(Continued)

FOREIGN PATENT DOCUMENTS

| | | |
|---|---|---|
| GB | 2437708 A | 11/2007 |
| WO | 03/057082 A1 | 7/2003 |
| WO | 2008/131195 A2 | 10/2008 |

OTHER PUBLICATIONS

Search Report and Written Opinion dated Apr. 25, 2012 from International Application No. PCT/US2012/020629, filed Jan. 9, 2012, 13 pages.

(Continued)

*Primary Examiner* — Ryan Severson
(74) *Attorney, Agent, or Firm* — Leanne Taveggia Farrell; Westman, Champlin & Koehler, P.A.

(57) ABSTRACT

A device performs a myringotomy and includes a main body, a hollow positioning member, a cutting edge for piercing a tympanic membrane, a protective sheath and an actuator. The main body is oriented along an axis and has a proximal end, a distal end and an outer surface. The main body includes an attachment hub for receiving components that provide suction. The hollow positioning member extends at least partially along the axis, is coupled to the main body and includes a distal end. The actuator is located on the main body and is configured to move the protective sheath from a first position that surrounds the cutting edge to a second position that exposes the cutting edge and from the second position back to the first position.

20 Claims, 17 Drawing Sheets

(56) References Cited

U.S. PATENT DOCUMENTS

| | | |
|---|---|---|
| 4,473,073 A | 9/1984 | Darnell |
| 4,580,568 A | 4/1986 | Gianturco |
| 4,695,275 A | 9/1987 | Bruce et al. |
| 4,744,792 A | 5/1988 | Sander et al. |
| 4,964,850 A | 10/1990 | Bouton et al. |
| 5,026,378 A | 6/1991 | Goldsmith, III |
| 5,053,040 A | 10/1991 | Goldsmith, III |
| 5,073,166 A | 12/1991 | Parks et al. |
| 5,139,502 A | 8/1992 | Berg et al. |
| 5,178,623 A | 1/1993 | Cinberg et al. |
| 5,207,685 A | 5/1993 | Cinberg et al. |
| 5,254,120 A | 10/1993 | Cinberg et al. |
| 5,466,239 A | 11/1995 | Cinberg et al. |
| 5,484,434 A | 1/1996 | Cartmell et al. |
| 5,496,329 A | 3/1996 | Reisinger |
| 5,566,094 A | 10/1996 | Kojima et al. |
| 5,578,053 A | 11/1996 | Yoon |
| 5,601,568 A | 2/1997 | Chevillon et al. |
| 5,643,280 A | 7/1997 | Del Rio et al. |
| 5,645,584 A | 7/1997 | Suyama |
| 5,665,094 A | 9/1997 | Goldenberg |
| 5,693,065 A | 12/1997 | Rains, III |
| D389,915 S | 1/1998 | Emerson et al. |
| 5,709,677 A | 1/1998 | Slatkine |
| 5,711,309 A | 1/1998 | Goldenberg |
| 5,916,150 A | 6/1999 | Sillman |
| 5,976,151 A | 11/1999 | Siegbahn |
| 6,027,532 A | 2/2000 | Hobeika |
| D439,337 S | 3/2001 | Jones |
| 6,245,077 B1 | 6/2001 | East et al. |
| 6,258,067 B1 | 7/2001 | Hill |
| D453,833 S | 2/2002 | Hess |
| 6,361,526 B1 | 3/2002 | Reisdorf et al. |
| 6,390,975 B1 | 5/2002 | Walls et al. |
| 6,406,453 B1 | 6/2002 | Goode et al. |
| 6,443,970 B1 | 9/2002 | Schulze et al. |
| 6,527,780 B1 | 3/2003 | Wallace et al. |
| 6,692,455 B2 | 2/2004 | Goode et al. |
| 6,695,861 B1 | 2/2004 | Rosenberg et al. |
| D490,152 S | 5/2004 | Myall et al. |
| 6,730,056 B1 | 5/2004 | Ghaem et al. |
| 6,770,080 B2 | 8/2004 | Kaplan et al. |
| 6,776,797 B1 | 8/2004 | Blom et al. |
| 6,936,023 B2 | 8/2005 | Goode et al. |
| 6,939,494 B2 | 9/2005 | Goode et al. |
| D521,641 S | 5/2006 | Reschke et al. |
| D538,936 S | 3/2007 | Böhmel et al. |
| 7,235,099 B1 | 6/2007 | Duncavage et al. |
| 7,410,480 B2 | 8/2008 | Muni et al. |
| 7,419,497 B2 | 9/2008 | Muni et al. |
| 7,704,259 B2 | 4/2010 | Kaplan et al. |
| D619,579 S | 7/2010 | Flores Rodrigues Vieira |
| 7,879,033 B2 | 2/2011 | Sartor et al. |
| 8,052,693 B2 | 11/2011 | Shahoian |
| D664,657 S | 7/2012 | Vieira et al. |
| 2002/0058899 A1 | 5/2002 | Goode et al. |
| 2003/0018291 A1 | 1/2003 | Hill et al. |
| 2005/0004520 A1 | 1/2005 | Lemoine et al. |
| 2005/0256450 A1* | 11/2005 | Palasis et al. .................. 604/82 |
| 2008/0051804 A1 | 2/2008 | Cottler et al. |
| 2008/0097295 A1 | 4/2008 | Makower et al. |
| 2008/0234708 A1 | 9/2008 | Houser et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2009/0209972 A1* | 8/2009 | Loushin et al. ............... 606/109 |
| 2010/0256653 A1 | 10/2010 | Kaplan et al. |
| 2011/0288559 A1 | 11/2011 | Shahoian |

OTHER PUBLICATIONS

Search Report and Written Opinion dated Oct. 1, 2009 from International application No. PCT/US2009/034648, filed Feb. 20, 2009, pp. 1-13.

Extended European Search Report dated Aug. 25, 2011 issued in European patent application No. 09713274.0, filed Feb. 20, 2009, pp. 1-7.

Communication from European Patent Office dated Sep. 13, 2011 issued in European patent application No. 09713274.0, filed Feb. 20, 2009, 1 page.

Communication dated Dec. 4, 2012 in Chinese Application No. 200980113954.0, filed Feb. 20, 2009, with English translation attached, 7 pages.

* cited by examiner

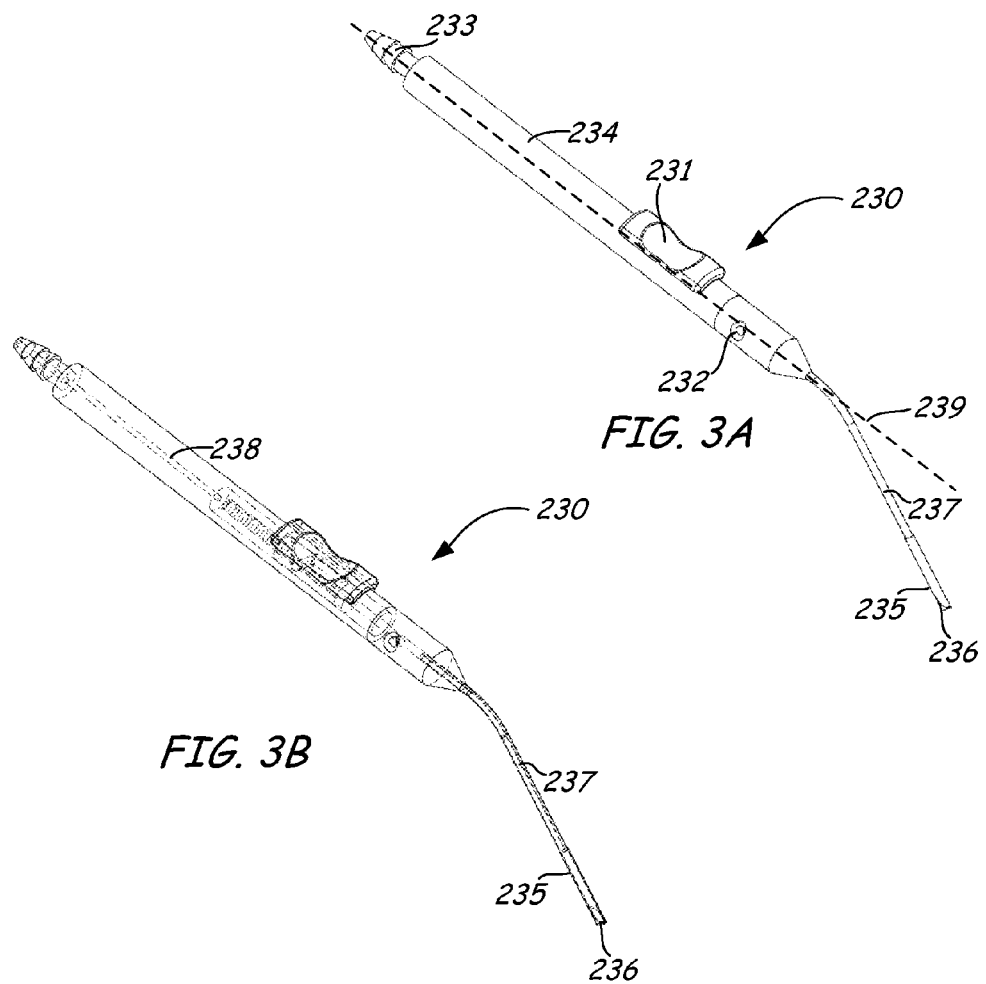
FIG. 3A
FIG. 3B
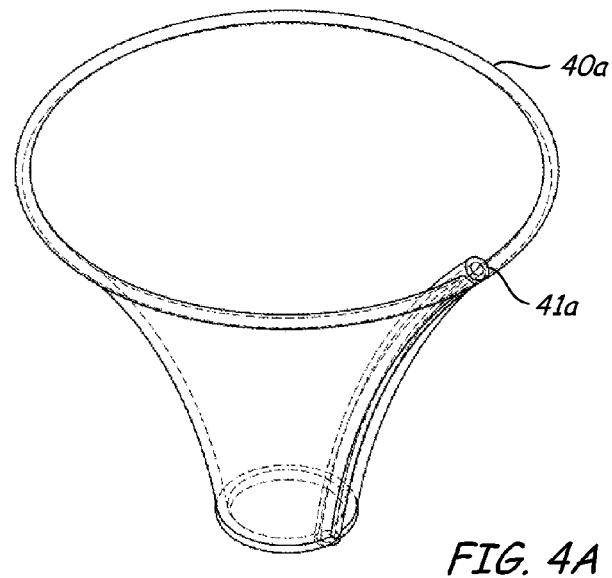
FIG. 4A

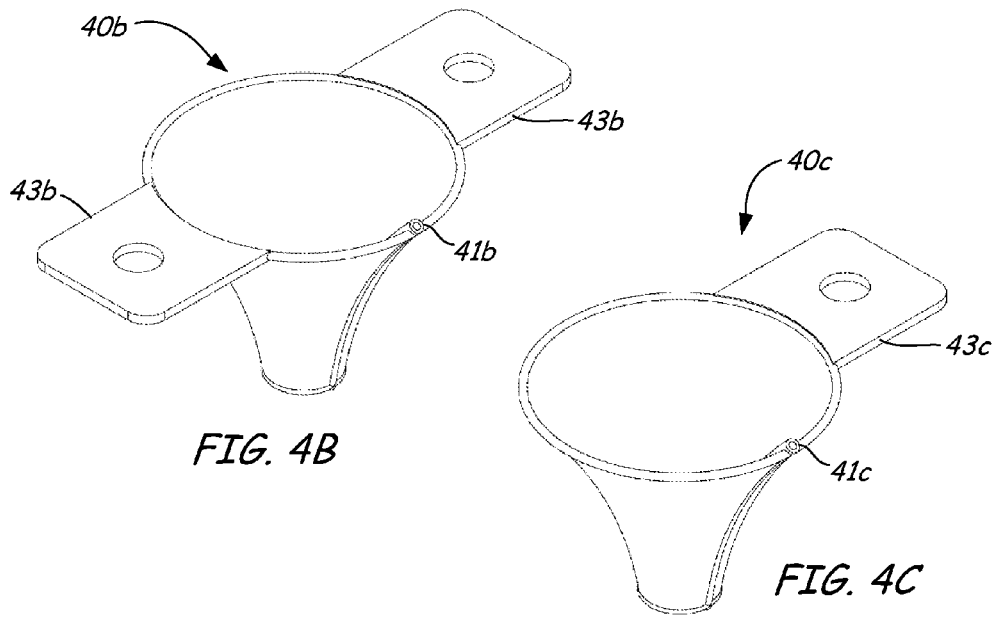
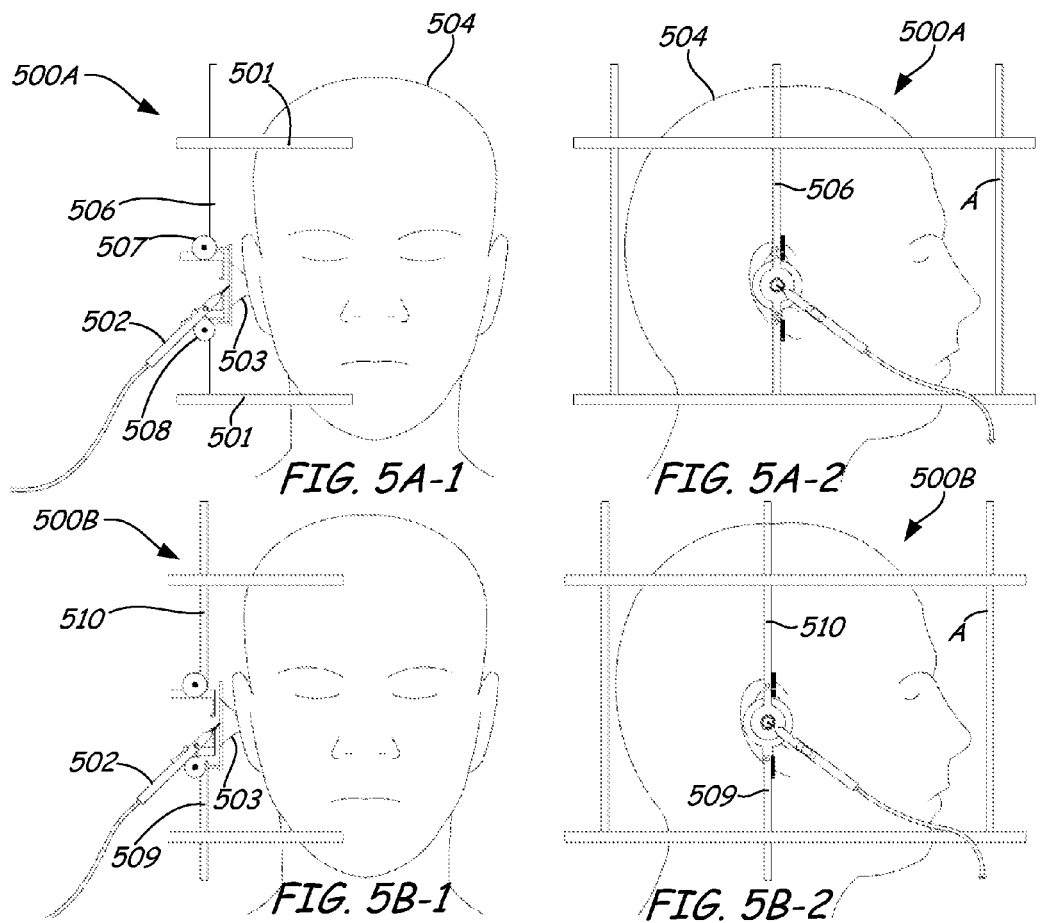

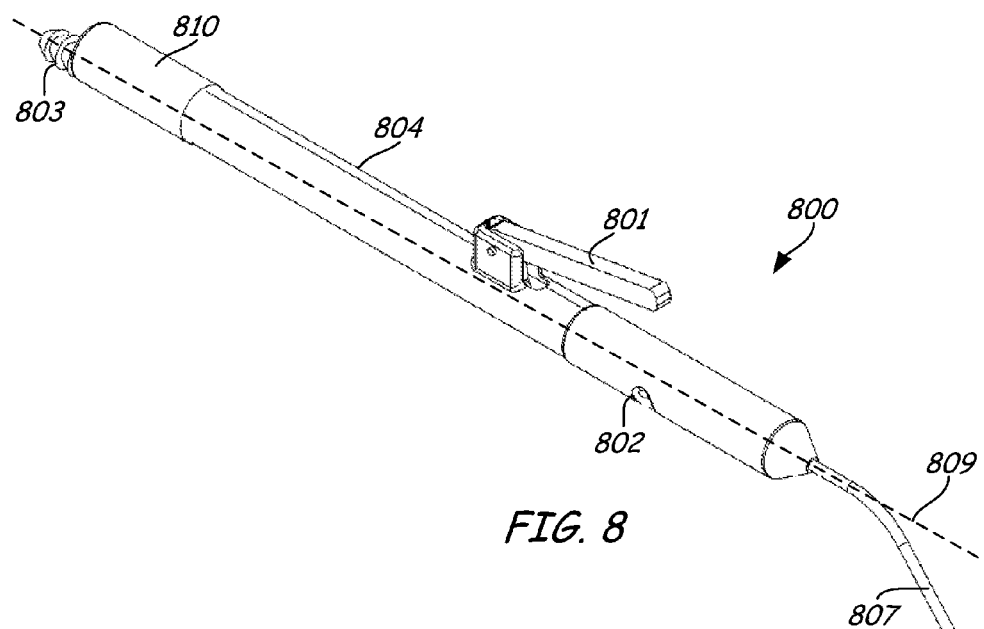
FIG. 8
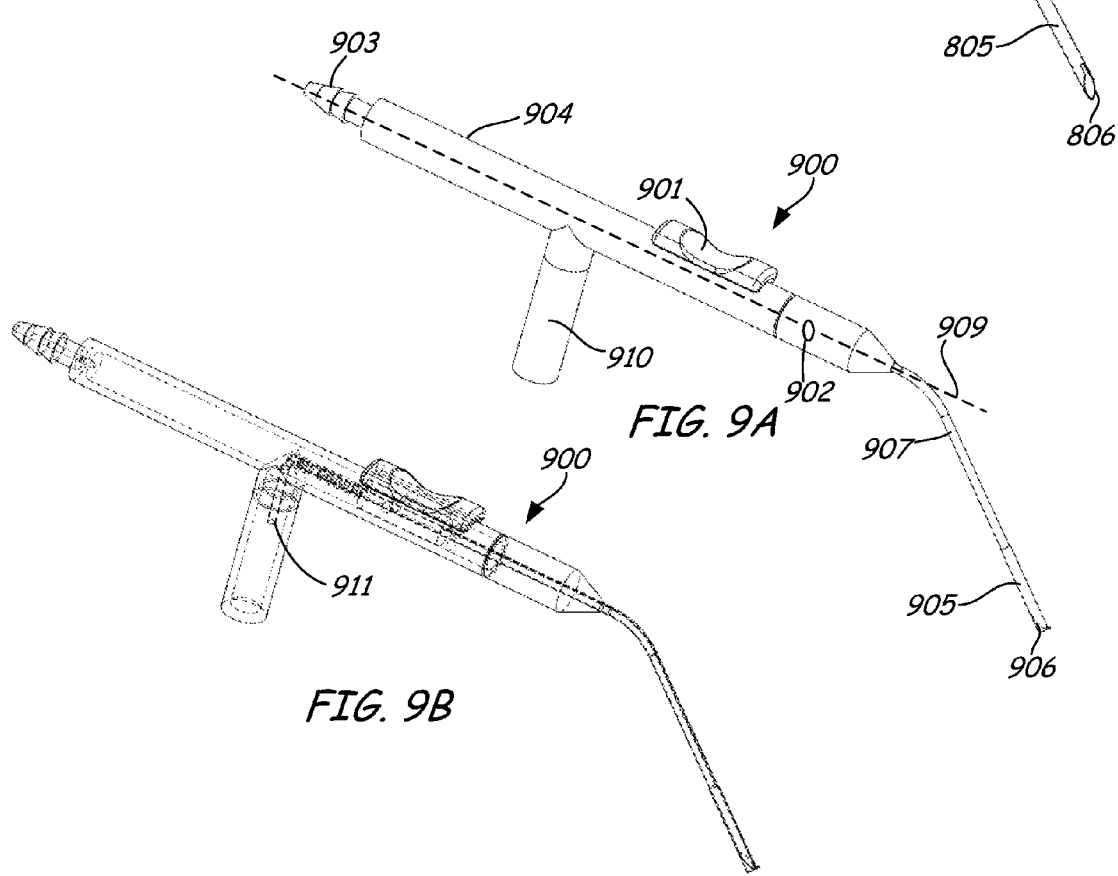
FIG. 9A
FIG. 9B

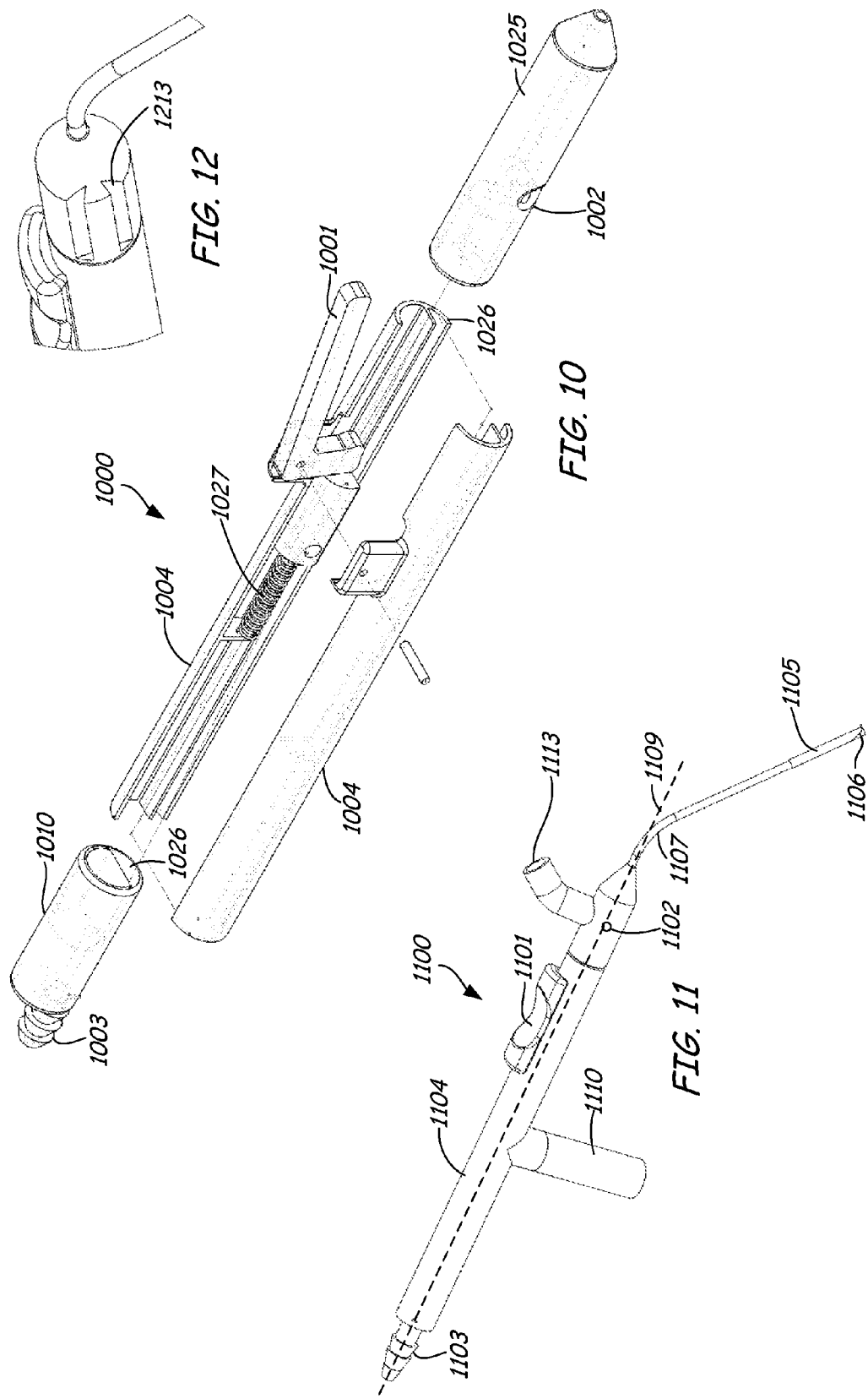

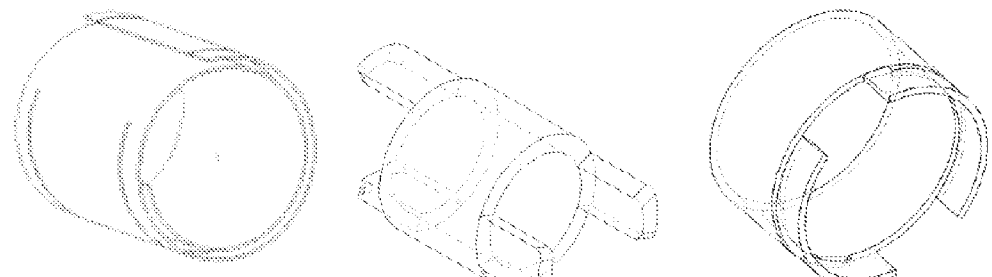
FIG. 16A  FIG. 16B  FIG. 16C
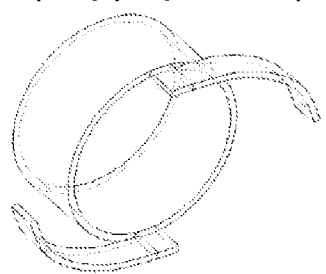 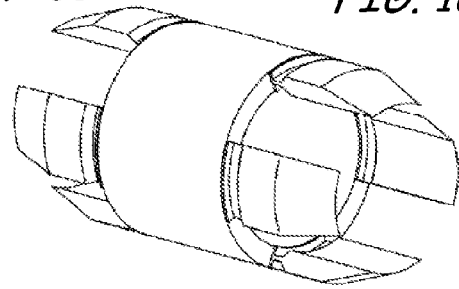
FIG. 16D  FIG. 16E
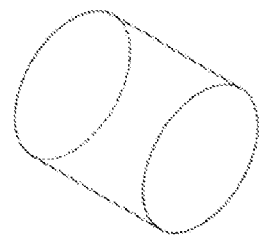 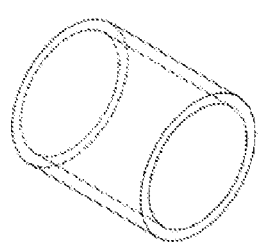
FIG. 16F  FIG. 16G
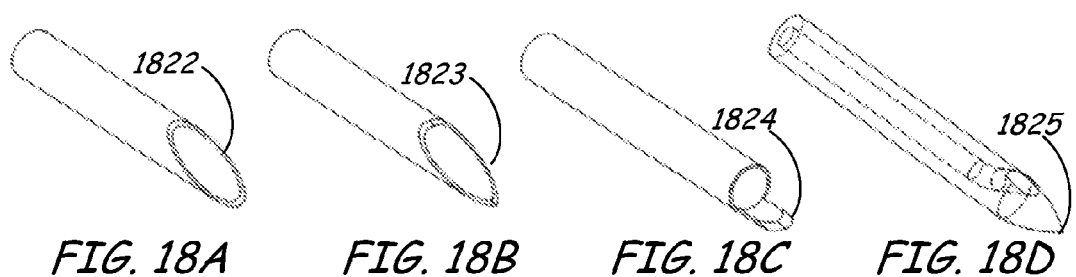
FIG. 18A  FIG. 18B  FIG. 18C  FIG. 18D

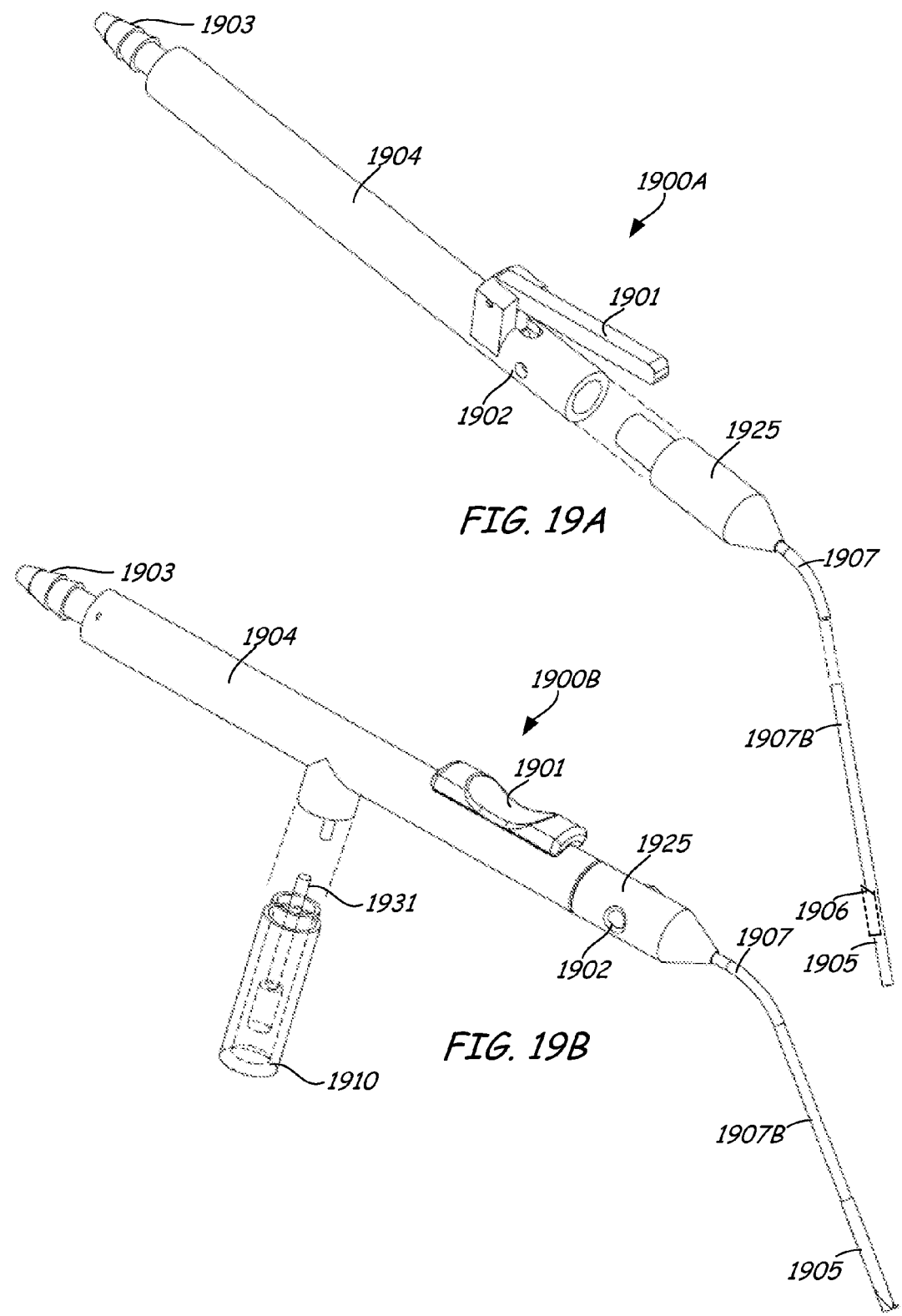

STABILIZATION SYSTEM AND ASPIRATION DEVICE WITH PROTECTED CUTTING EDGE

CROSS-REFERENCE TO RELATED APPLICATION

The present application is based on and claims the benefit of U.S. provisional patent application Ser. No. 61/430,758, filed Jan. 7, 2011, the content of which is hereby incorporated by reference in its entirety.

BACKGROUND

Otitis media (OM) is a common infection in the pediatric population often treated with antimicrobial therapy. If the infection persists or becomes chronic, medical practitioners can use surgical invention, such as performing a procedure called a myringotomy or tympanocentesis. A myringotomy is the procedure of incising or puncturing the eardrum or tympanic membrane. The myringotomy is meant to promote healing and relieve discomfort by allowing the fluid trapped within the middle ear to drain. A further procedure that can be performed is the insertion of a tympanostomy tube into the opening in the eardrum created by the myringotomy. The tube placement keeps the middle ear aerated for a prolonged period of time and promotes prolonged relief.

The discussion above is merely provided for general background information and is not intended to be used as an aid in determining the scope of the claimed subject matter.

SUMMARY

A device performs a myringotomy and includes a main body, a hollow positioning member, a cutting edge for piercing a tympanic membrane, a protective sheath and an actuator. The main body is oriented along an axis having a proximal end, a distal end and an outer surface. The main body includes an attachment hub for receiving components that provide suction. The hollow positioning member extends at least partially along the axis, is coupled to the main body and includes a distal end. The actuator is located on the main body and is configured to move the protective sheath from a first position that surrounds the cutting edge to a second position that exposes the cutting edge and from the second position back to the first position.

To perform the myringotomy, at least portions of the positioning member, the cutting edge and the protective sheath, which is covering the cutting edge, are manually inserted into an ear canal of a patient using an outer surface of the main body as a handle. The protective sheath is actuated while the positioning member and the cutting edge remain in place such that the protective sheath slides relative to and along the positioning member to expose the cutting edge. The positioning member, the cutting edge and the actuated protective sheath are manually advanced using the handle such that the cutting edge pierces the tympanic membrane. The positioning member, the cutting edge and the actuated protective sheath are manually retracted such that the cutting edge is again located the spaced distance from the tympanic membrane. The protective sheath is actuated while the positioning member and the cutting edge remain in place such that the protective sheath slides relative to and along the positioning member to again cover the cutting edge. The positioning member, the cutting edge and the protective sheath are manually extracted from the ear canal using the handle.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIGS. 3A and 3B illustrate an aspiration device comprising a handle, a cutting portion, a safety portion, and a sliding means of manipulating the safety portion under another embodiment.

FIGS. 4A, 4B, and 4C illustrate embodiments of a speculum-like device used to aid in visualizing down the ear canal during the creation of a myringotomy or during ear tube placement.

FIGS. 5A-1, 5A-2, 5B-1, 5B-2 and 5C illustrate front and side views of various embodiments of a stabilization component for use with the aspiration device.

FIG. 8 illustrates an aspiration device under yet another embodiment comprising a handle, a cutting portion, a safety portion, a lever actuated means of manipulating the safety portion, and a sample chamber for collecting aspirated fluids for microbiological analysis.

FIGS. 9A and 9B illustrate an aspiration device under yet another embodiment comprising a handle, a cutting portion, a safety portion, a lever actuated means of manipulating the safety portion, and an alternative embodiment of a sample chamber for collecting aspirated fluids for microbiological analysis.

FIG. 10 illustrates an exploded view of an aspiration device comprising a handle, a cutting portion, a safety portion, a lever actuated means of manipulating the safety portion, and a sample chamber for collecting aspirated fluids for microbiological analysis.

FIG. 11 illustrates an aspiration device under yet another embodiment having a mechanical interface for mechanically coupling to a stabilization component.

FIG. 12 illustrates an alternative embodiment of aspiration device having of a mechanical interface for mechanically coupling to a stabilization component.

FIGS. 16A-16G illustrate various embodiments of ear tubes or prosthetics that the system could deploy across the tympanic membrane.

FIGS. 18A-18D illustrate various embodiments of cutting edges that could be used to create an incision in a membrane.

FIGS. 19A and 19B illustrate embodiments where the sampling portion, a swab located inside the sampling portion, the nose portion, or a portion of the placement member or aspiration conduit can be removed from the device for accessing or transporting aspirated fluids.

DETAILED DESCRIPTION

Figure 1:
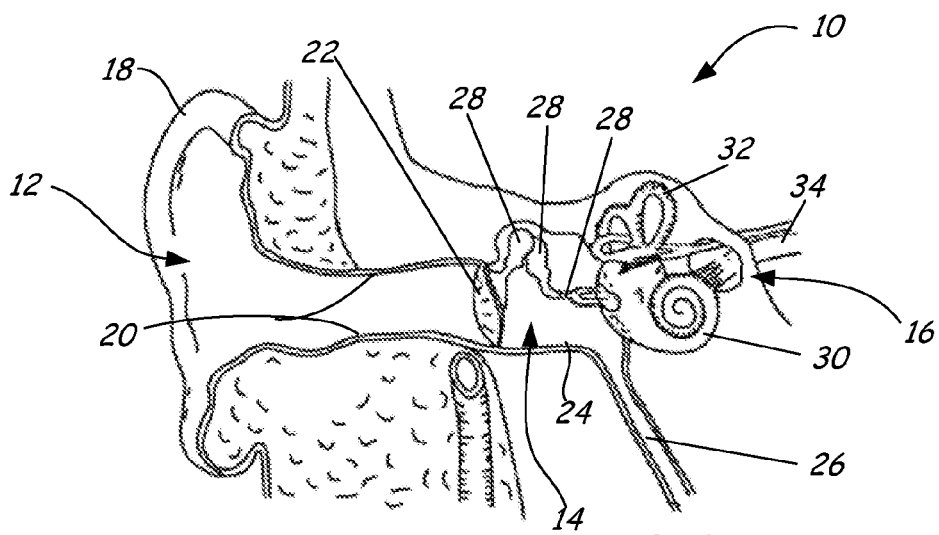
FIG. 1 is a simplified diagrammatic view of an ear.

Embodiments described are directed to various devices and systems for creating an incision in a membrane or tissue of a body, such as an eardrum or tympanic membrane, aspirating fluid behind the tissue and collecting the fluid. In particular, embodiments describe a manually operable device capable of safely passing a cutting edge down the ear canal of a patient, creating a myringotomy, and aspirating and collecting a fluid sample from the middle ear. In one further embodiment, a prosthetic, such as a tympanostomy tube can be placed in the myringotomy to keep the opening from closing. Specific details regarding components and methods of inserting a tympanostomy tube or ear tube in the myringotomy are described in detail in U.S. patent application Ser. No. 12/389,552 published as U.S. 2009/0209972 on Aug. 20, 2009, which is hereby incorporated by reference in its entirety. Such tympanosotomy tubes and components for inserting a tympanosotomy tube can be included in these and other disclosed embodiments.

Described embodiments also allow the entire procedure to be performed under direct visualization without additional magnification beyond that provided by a normal operating otoscope or similar instrument. However, embodiments can be adapted to provide alternative visualization tools, such as fiber optic viewing scopes.

More specifically, described embodiments include a reversibly positionable protective sheath arrayed over the cutting portion or cutting edge to prevent accidental trauma while it is placed into position for creating an incision, cut or puncture and to facilitate safe placement of the cutting edge at a given depth within the opening or passage in the membrane created by the myringotomy. To create the incision, the user moves the sheath to allow for the cutting edge to be exposed via an actuator, and upon creation of the incision, the sheath can be repositioned again to protect the patient from the cutting edge. Once an incision or puncture has been made, the application of negative pressure can be applied to aspirate fluids for pain relief or for diagnostic purposes. Because the cutting component of the device is not exposed during insertion into or retraction from the ear canal, placement of the device in proximity to the tympanic membrane prior to create a myringotomy can be done manually. In one embodiment, once correct placement of the protected cutting component is achieved, a stabilization component that limits the axial travel of the cutting device toward the patient can be deployed, or locked in place, ensuring that tissues or structures located behind the tympanic membrane aren't injured due to inadvertent patient movement. After the myringotomy is formed, the cutting component is again protected before the stabilization component is released, allowing retraction of the device out of the ear canal. A device that creates an incision, aspirates fluid and collects fluid without the risk of accidental trauma from the cutting component allows clinicians to provide symptom relief and obtain better diagnostic information.

Otitis media (OM) is the most common infection requiring antimicrobial therapy in the pediatric population. In 1990, there were over 25 million office visits for acute OM with over 20 million antibiotic prescriptions (Clinical Practice Guideline: Diagnosis and Management of Acute Otitis Media, Subcommittee on Management of Acute Otitis Media, American Academy of Pediatrics and American Academy of Family Physicians, 2004). In developing countries, the incidence of OM is a major contributor to childhood hearing loss and mortality due to intracranial complications. In spite of frequent use of antibiotics, morbidity and decreased quality of life associated with OM is significant.

Prior to the antibiotic era, medical practitioners commonly treated middle ear infections by incising or puncturing the eardrum with a handheld probe. This procedure, called myringotomy or tympanocentesis, was meant to promote healing and relieve discomfort by allowing the fluid to drain into the external ear canal. In the latter half of the $20^{th}$ century, as antibiotics gained acceptance for the treatment of ear infections, tympanocentesis became less and less common.

Current therapy for OM includes close observation ("watch and wait"), antibiotic therapy, and surgical intervention such as myringotomy with tympanostomy tube placement. The liberal use of antimicrobials for the treatment of OM has significantly increased the incidence of antibiotic resistant bacteria. The incidence of antibiotic resistance to penicillins and trimethoprim-sulfamethoxazole ranges from 50-90%, depending on the geographic location in the US. In some patients with acute OM, there is evidence of methacillin resistant staphylococcus aureus (MRSA) bacteria even in previously healthy patients.

Because of the emergence of antibiotic resistant bacteria, determining the bacterial etiology of an ear infection is necessary to ensure appropriate medical treatment. In middle ear infections, bacterial identification can be made by obtaining a sample of middle ear fluid for culture analysis via tympanocentesis. Tympanocentesis also provides immediate symptom and pain relief and allows ventilation and drainage of the middle ear. In spite of the risks associated with the procedure, tympanocentesis is regaining recognition as a necessary tool in the treatment of ear infections.

FIG. 1 illustrates a system of organs in an ear 10 of a body that enables a person to detect sound. Ear 10 is able to change sound pressure waves into a signal of nerve impulses to be processed by the brain. Ear 10 includes an outer ear 12, a middle ear 14 and an inner ear 16. Outer ear 12 collects sound and includes the pinna 18, the ear canal 20 and an outer most layer of the ear drum or tympanic membrane 22. Pinna 18 helps direct sound through ear canal 20 to tympanic membrane 22. Middle ear 14 includes an air-filled cavity 24 having an opening for the Eustachian tube 26 that is located behind tympanic membrane 22. Middle ear 14 also includes ossicle bones 28. Inner ear 16 includes the fluid-filled cochlea 30 and the semicircular canals 32. Cochlea 30 is the auditory portion of the inner ear, while semicircular canals 32 are attuned to both gravity and motion. The ossicle bones 28 transmit sound from the air in cavity 24 to cochlea 30. Fluid in cochlea 30 moves in response to the vibrations coming from middle ear 14. The motion of the fluid is converted to electrical impulses, which travel along the auditory nerve 34 to structures in the brainstem for further processing. Eustachian tube 26 couples cavity 24 of middle ear 14 to the nose and mouth of a human. In a normal state, Eustachian tube 26 is collapsed. However, Eustachian tube 26 can open and close to equalize pressure in cavity 24.

Severe pain and an infection of the middle ear 14 can result upon build-up of fluid and increased pressure in cavity 24. Children are often prone to infections of middle ear 14 because of their underdeveloped Eustachian tube 26. A myringotomy is a surgical procedure in which a tiny incision is created in tympanic membrane 22 to relieve pressure caused by the excessive buildup of fluid due to an infection of the middle ear 14. If a patient requires a myringotomy, this generally suggests that Eustachian tube 26 is either partially or completely obstructed and is not able to perform its proper functions In some cases, besides making an incision in tympanic membrane 22, fluids can be aspirated from the middle ear to provide pain relief or for making a microbiologic assessment of the etiology of the infection. However, in the confined space of ear canal 20, especially an ear canal of a child, the risk of inadvertent trauma exists while positioning the cutting portion. In one example, a child may move during the procedure, resulting in a cut in the ear canal which can result in bleeding that is difficult to stop. Although this relatively brief procedure can be performed on an outpatient basis, clinicians may be reluctant to perform the operation without putting the patient under anesthesia because of the risk of cutting the ear canal if the patient moves during the procedure. A device that can alleviate these disadvantages can greatly enhance patient comfort and provide improved information for the subsequent treatment, such as what antibiotics to prescribe, while simultaneously simplifying the procedure for physicians.

As discussed above, embodiments described are directed towards devices, systems and procedures for creating an incision and aspirating fluids from a membrane or tissue in the body, such as tympanic membrane 22. It should be realized, though, that embodiments described can be used to incise and aspirate fluids from any anatomical structure of the body whether the opening is naturally occurring or surgically created. In addition, embodiments are not limited to just ear applications, but could provide communication between any two areas in a body separated by a membrane or barrier. In addition, while most of the description of the aspiration device relates to tympanocentesis and procedures involving the ear canal and tympanic membrane, embodiments of the apparatus described can be used for the aspiration and collection or evacuation of fluids from the sinus cavities, abcesses, or other body cavities.

Figure 2A:
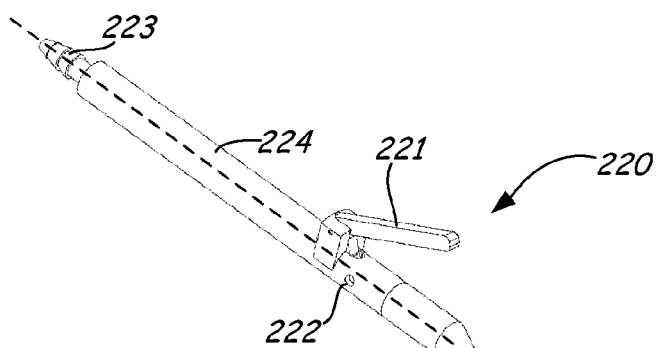
FIGS. 2A and 2B illustrate an aspiration device comprising a handle, a cutting portion, a safety portion, and a lever actuated means of manipulating the safety portion under one embodiment.
Figure 2B:
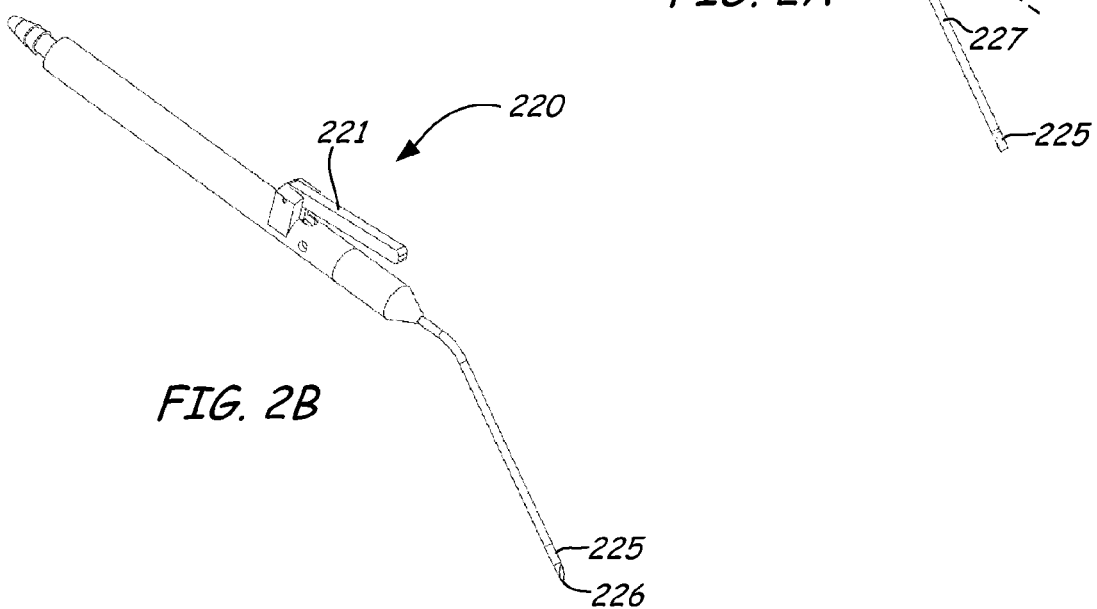

FIGS. 2A and 2B illustrate a handheld aspiration device 220 that can be disposable. The aspiration device 220 comprises a cylindrical housing or main body 224 that includes an outer surface that provides a handle and is oriented along a central axis 229, a hollow positioning member 227 that extends at least partially along axis 229, a cutting portion or cutting edge 226 located on the distal end of the positioning member, a moveable protective sheath 225 positioned over at least a portion of the positioning member 227, and an actuation member 221 attached to the housing that can reversibly position the moveable sheath such that the cutting portion or edge can be one of exposed or shielded. FIGS. 2A and 2B illustrate a lever-type or squeeze-type actuator. In FIG. 2A, the actuation member 221 is in a neutral position such that the cutting portion or edge 226 is covered by the protective sheath 225. In FIG. 2B, the actuation member 221 is depressed such that the cutting portion 226 is exposed. Also shown is an attachment hub 223 for attaching or receiving a source of negative pressure to allow the device to aspirate fluids, and a weep-hole style actuator 222 to allow the user to direct the negative pressure to the distal end of the positioning member 227 when desired. In cases where negative pressure is supplied by a vacuum pump, movement of the protective components could be done with vacuum. In one embodiment, actuation force provided by the user moves or slidably moves the protective portion or sheath 225 to expose the cutting portion or edge 226 of positioning member 227, and a constant return force, for example in the form of a spring, returns the protective portion or sheath 225 to it's neutral position of covering the cutting portion or edge 226. Of course, the opposite behavior could also be implemented.

Main body 224 can be a reusable component, or a single use disposable component. It can be made from translucent or opaque plastic or a metal such as stainless steel. It can consist of a single part or of multiple components. In addition, because it is desirable that the positioning member 227, cutting edge 226 and sheath 225 are sterile, in one embodiment positioning member 227, including cutting edge 226, and sheath 225 are removable and disposable. In an alternative embodiment, components 227, 226 and 225 can be sterilized in an autoclave or other facility-based sterilization methods, or by a reprocessor.

As described above and in one embodiment, the housing 224 includes an attachment hub 223 for connecting to a source of negative pressure. For example, attachment hub 223 can connect to a barbed fitting for the attachment of suction tubing which is connected to a vacuum source. In another example, housing 224 may also have an internal volume that can achieve and sustain a vacuum, such as a syringe-style arrangement where a plunger is pulled back and locked in place to create a vacuum. In yet another example, the housing 224 may also contain internal conduits and passageways that allow the user to selectively apply negative pressure to the positioning member 227 so that fluids can be aspirated into the housing 224.

The actuator member 221 that the user interfaces with to expose/protect the cutting portion or edge 226 of position member 227 can also be used to control the application of negative pressure, or suction, to the distal end of the positioning member 227, or sampling point. Control of suction at the sampling point is necessary to ensure that aspirated fluids are collected at the desired location. For example, when used for sampling fluids from a middle ear infection, suction should only be applied at the sampling point once the incision has been made in the tympanic membrane and the sampling point is in contact with the fluids located in the middle ear. Suction applied continuously could provide erroneous information by aspirating fluids or bacteria from the ear canal. Furthermore, in cases where the source of vacuum is limited, for example, by generating vacuum in a volume with a syringe type mechanism, the suction must be judiciously applied to achieve the desired degree of aspiration.

As illustrated in FIGS. 2A and 2B, positioning member 227 is bent at an angle from the axially alignment of main body 224 along axis 229. The use of a bent positioning member 227 provides unobstructed sight lines for the user. In other words, main body 224 or the handle of main body 224 is not in a direct line with the distal end of positioning member 227, which enhances direct visualization during insertion of the device. In such a configuration, actuator member or mechanism 221 transmits the necessary force around a bend. In one embodiment, a flexible actuating member connecting the actuation mechanism 221 to protective sheath 225 can be employed. For example, a flexible two force member, such as a wire, can be used. This flexible member can be restrained within an inflexible sheath that follows the bend of the positioning member 227, for example a rigid hollow tube that makes up the positioning member 227 or closely approximates it, and in doing so transmits the push/pull force applied by the user directly to the safety portion. Other "two force" mechanical components or a mechanical apparatus capable of achieving a similar result, such as a pair of cables or cords or a looped cord could also be used to transmit the actuation motion around a bend. For example, the flexible actuator for the protective sheath 227 may consist of a rigid wire or plastic rod. This rigid wire or rod could be located completely outside of the positioning member, or could be routed inside the positioning member, or could be routed inside the positioning member and transition to outside the member at some point for attachment to the protective portion. Alternatively, a flexible polymer tube placed over the entire length of the positioning member and able to move axially along its length could function both as a flexible actuator, capable of moving axially along a bend, and as the protective portion, serving as a safety sheath over the cutting portion of the device.

FIGS. 3A and 3B illustrate another embodiment of a handheld aspiration device 30 that can be disposable. The aspiration device 230 of FIGS. 3A and 3B comprises a housing or main body 234 that includes an outer surface that provides a handle and is oriented along a central axis 239, a hollow positioning member 237 that extends at least partially along axis 239, a cutting portion or cutting edge 236 located on the distal end of the positioning member, a moveable protective sheath 235 positioned over at least a portion of the positioning member 237, and a sliding actuation member 231 attached to the housing that can reversibly position the sheath 235 such that the cutting portion or cutting edge can be exposed or shielded. The actuator member 231 that actuates the protective portion 235 includes a 'slider' type trigger, actuated by the thumb or forefinger of the user. A 'slider' type trigger provides a great degree of control and stability. In FIG. 3A the cutting portion or edge 236 is covered by the protective sheath 235. In FIG. 3B the actuation member 231 is slid along axis 239 of main body 234 to therefore slidably move sheath 235 such that the cutting portion or edge 236 is exposed. Also shown is an attachment hub 233 for attaching a source of negative pressure to allow the device to aspirate fluids, and a weep-hole style actuator 232 to allow the user to direct the negative pressure to the end of the positioning member 237 when desired. FIG. 3B also shows the internal passages 238 of the device capable of delivering negative pressure along the housing 234, past the weep-hole 232 and down the positioning member 237 for aspiration of fluids after creation of a myringotomy. In cases where negative pressure is supplied by a vacuum pump, movement of the protective components could be done with vacuum. In one embodiment, actuation force provided by the user moves the protective portion or sheath 235 to expose the cutting portion or edge 236, and a constant return force, for example in the form of a spring, returns the protective portion to it's neutral position, covering the cutting portion. Of course, the opposite behavior could also be implemented.

FIG. 4A illustrates a speculum-like device 40a that can be used to enhance direct visualization by the user of an aspiration device that is inserted into an ear canal of a patient. Speculum-like device 40a can be similar to aural speculums, and can include attachment means for connecting to a stabilization component so that speculum 40a can be aligned by the user and held in position to free up the user's hand. In one embodiment, speculum-like device 40a includes a passage or means of passing or attaching a visualization aid such as a fiber optic scope 41a without negatively impacting direct visualization, reducing the cross sectional area of the speculum available for passing devices used for performing a myringontomy or ear tube insertion, or blocking access to the ear canal under one embodiment. The passage forms a cone-type shape where a first circular end tapers to a second circular end. FIGS. 4B and 4C illustrate embodiments of speculum-like devices 40b and 40c that also include passages or means of passing or attaching a visualization aid such as a fiber optic scope 41b and 41c without blocking access to the ear canal. Again, the passages form cone-type shapes where a first circular end tapers to a second circular end.

Another embodiment of the speculum-like component 40a includes a means of sealing the component to the patient's ear canal sufficiently to allow tympanometry to be performed. The application and measurement of pressure could be made solely with the speculum-like component, with the handle component, or a combination of both. For example, the speculum could seal against the patient, and include a means of applying pressure via an integral air channel or tube, while the handle component with a pressure sensing means and a plug component could seal to the inner surface of the speculum. Pressure could be applied to the ear canal and tympanic membrane across the speculum-like component and measured via the handle component attached to an appropriate pressure sensing means.

Speculum devices 40b and 40c also include one or more integral attachment points 43b and 43c that allow the speculum to interface with a stabilization component temporarily to allow the user to position the speculum, lock it into place and free-up a hand for placing the handheld aspiration device, for example. In FIG. 4B, speculum device 40b includes a pair of attachment points 43b. The pair of attachment points 43b are positioned on opposing sides of the first circular end and include through holes for receiving fasteners to be coupled to a stabilization component. In FIG. 4C, speculum device 40c includes a single attachment point 43c. Attachment point 43c is positioned along the circumference of the first circular end and includes a through hole for receiving a fastener to be coupled to a stabilization component.

FIGS. 5A-1, 5A-2, 5B-1, 5B-2, 5C, 6A, 6B, 7A and 7B all illustrate various embodiments of stabilization devices or systems. A stabilization system or stabilization device can be positioned against a patient's body, or a patient's body can be positioned against the stabilization system, which is attached to a speculum-like component, a hand held aspiration device, or both. The attachment of the aspiration device to the stabilization component, or to the speculum which is attached to the stabilization component, limits the axial movement of such devices toward the patient. In the creation of a myringotomy or placement of an ear tube this limitation in penetration depth prevents the device from damaging tissues behind the tympanic membrane.

A stabilization system or device allows manual manipulation of the handle of the aspiration device in 3, 4, or 5-axes, depending on the design, to allow the user to easily place the positioning member in the correct orientation and proximity to the tympanic membrane for creating a myringotomy with or without the placement of an ear tube or other component in the myringotomy. Once the user has correctly positioned the device, a locking means, or alternative means of preventing or limiting further movement in all axes, is actuated. Limited movement in the axis toward the patient, in a range of 0-4 millimeters in the case of tympanocentesis or ear tube placement, is still allowed so that the desired procedure can be performed. Because the entire system is stabilized to the patient head, or the patient head is restrained by the stabilizer, unintended relative movement between the patient and the cutting edge cannot occur.

FIG. 5A-1 illustrates a front view of a stabilization system 500A located proximal to a patient's head 504 and FIG. 5A-2 illustrates a side view of the stabilization system 500A and patient's head 504 illustrated in FIG. 5A-1. In FIG. 5A-1, a front bar A is removed for purposes of clarity. Patient contacting members 501 are positioned to hold device-holding members 506 in position over the patient's ear canal. Speculum-like device 503 and handheld aspiration device 502 are shown attached to members 506.

Mechanical adjusters 507 and 508 allow motion in 3, 4, or 5 axes such that the positioning member of aspiration device 502 can be accurately positioned for the creation of a myringotomy. Once the aspiration device 502 is positioned, the position adjustments 507 and 508 of stabilization system 500 can be lock limited to prevent motion in one or more axes and to prevent injury in the case where the patient's head moves during the procedure. In FIGS. 5A-1 and 5A-2, speculum 503 and handheld aspiration device 502 are both fixed to members 506 and therefore fixed relative to each other by being connected to the fixed members 506 of the stabilization system 500.

In another embodiment, FIG. 5B-1 illustrates a front view of stabilization system 500B proximal the patient's head 504 and FIG. 5B-2 illustrates a side view of the stabilization system 500B and patient's head 504 illustrated in FIG. 5B-1. In FIG. 5B-1, bar A is removed for purposes of clarity. Patient contacting members 501 are positioned to hold device-holding members 509 and 510 in position over the patient's ear canal. Speculum-like device 503 is shown attached to member 509 while handheld aspiration device 502 is shown removably attached to member 510. Mechanical adjusters 507 and 508 allow motion in 3, 4, or 5 axes such that the positioning member of the aspiration device 502 can be accurately positioned for the creation of a myringotomy. Once positioned, the position adjustments 507 and 508 can be lock limited to prevent motion in one or more axes and to prevent injury in the case where the patients head moves during the procedure. In FIGS. 5B-1 and 5B-2, speculum 503 and handheld aspiration device 502 are connected to different members 509 and 510, respectively, of the stabilization system 500.

Figure 5C:
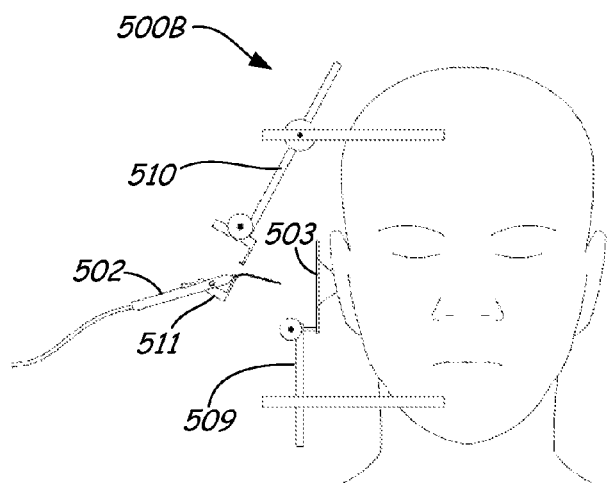

FIG. 5C shows stabilization system 500B as is illustrated in FIGS. 5B-1 and 5B-2, but with member 510 rotated outward to illustrate the independent movement of handheld aspiration device 502 and speculum 503. In addition, aspiration device 502 includes a platform 511 that is coupled to device 502. In FIGS. 5A-1 and 5A-2, platform 511 attaches to member 506. In FIGS. 5B-1, 5B-2 and 5C, platform 511 attaches to member 510.

Figure 6A:
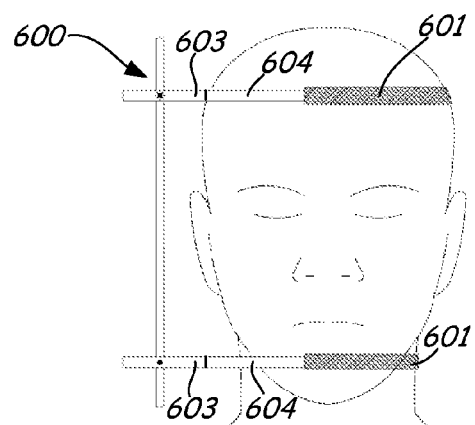
FIGS. 6A and 6B illustrate front and top views of a stabilization system using straps to secure the stabilization device to the patient, or the patient to the stabilization device under another embodiment.
Figure 6B:
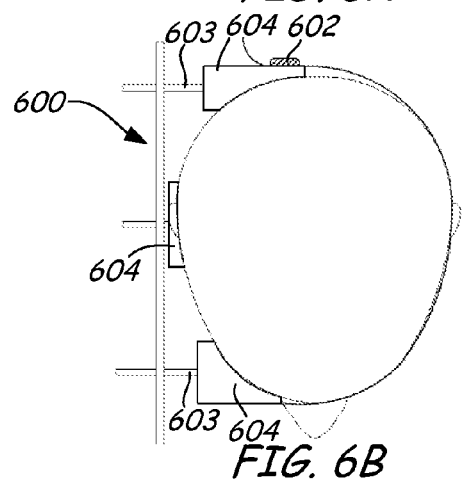

FIG. 6A illustrates a front view of a stabilization system 600 and FIG. 6B illustrates a top view of stabilization system 600 under yet another embodiment. Stabilization system 600 attaches to a patient's head using straps 601. Patient contacting pads 604 physically stabilize the system in relation to the patient's head, straps 601 prevent any relative movement, and tightening mechanisms 602, in conjunction with adjustable members 603, allow the system 600 to fit many different sized patients.

Figure 7A:
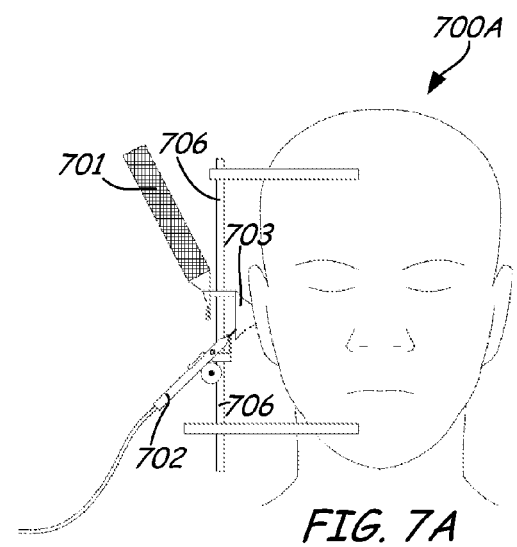
FIGS. 7A and 7B illustrate various embodiments of the stabilization component used in conjunction with an otoscope type surgical instrument.

FIG. 7A shows a stabilization system 700A being used in conjunction with an attached or fixed handheld aspiration device 702 and an otoscope 701 being operated freehand under yet another embodiment. In this embodiment, the speculum 703, which is not coupled to any fixed member of the stabilization system, is coupled to the operating otoscope 701 so that both components are operated freehanded. In other words, operating otoscope 701 is held freehanded along with speculum 703 while aspiration device 702 is attached to stabilizing member or members 706 with a locking mechanism for limiting axial movement of aspiration device 702 toward the patient's head when the cutting portion or edge of the aspiration device is exposed. In this way, operating otoscope 701 can be used for magnification and lighting purposes in conjunction with the stabilization systems 500A and 500B shown in FIGS. 5A-1 and 5A-2 or 5B-1, 5B-2 and 5C, where the speculum 503 is attached to members of the stabilization system 500.

Figure 7B:
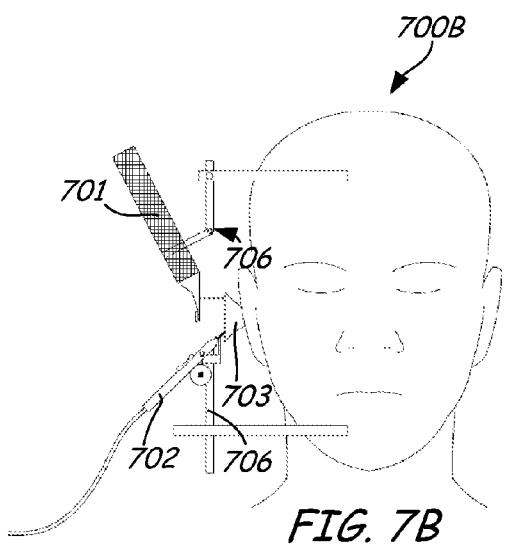

Under yet another embodiment, FIG. 7B shows a stabilization system 700B being used in conjunction with attached handheld aspiration device 703 and an attached operating otoscope 701. In this embodiment, the speculum 703 is attached to the operating otoscope 701, which is also attached to the stabilization system 700B. In other words, operating otoscope 701 is attached to stabilizing member or members 706 as well as the aspiration device 702 with a locking mechanism for limiting axial movement of device 702 toward the patient's head when the cutting portion or edge of the aspiration device is exposed.

As discussed in regards to FIGS. 2A, 2B, 3A and 3B, described embodiments of the aspiration device can include a means of applying negative pressure, or suction, for aspirating fluids, and may additionally include a reservoir for collecting said fluids for subsequent diagnostic testing. A suction modulation means, such as a 'weep hole' that limits suction delivered to the end of the device until it is blocked by the user, is provided to allow the user to select the location where aspirated fluid samples are collected. In embodiments with a weep hole, two may be present, one on each side of the device to allow ambidextrous (right or left handed) use, with the provision of a removable plug that can be placed in the weep hole not used.

In another embodiment, a check valve or suitable alternative to a weep hole could be used to control the amount of suction applied to the end of the device for aspirating fluid. The actuation of the check valve could be achieved using the same actuation means for exposing the cutting edge. For example, sliding an actuator axially along the device handle in one direction could deploy the cutting edge, while sliding the actuator axially in the other direction could open a check valve allowing suction to be applied at the end of the positioning member.

In another embodiment, the device includes a 'flash window' or alternative visual indication that a fluid sample was successfully obtained. The device may include an integral sterile sampling chamber where aspirated fluid is deposited. This sampling chamber may be removable from the device and used for transporting the sample for subsequent analysis, or may simply allow access for swabbing or other means of sample transfer to a sterile sample container for transport. In yet another embodiment, the sampling container contains an integral swab for transferring fluids to a transport vial.

Means of applying negative pressure can include an attachment means to apply 'wall suction' or a portable suction generator to the device. Alternative embodiments include a means, such as a luer type connection, for connecting the handheld device to a squeeze bulb or syringe which can be used to generate suction. Additional embodiments include a check valve to 'store' the negative pressure generated by a squeeze bulb or syringe, and a means of allowing the user to actuate the check valve to apply that negative pressure to aspirate fluids. A device capable of using mechanically generated negative pressure could have widespread application in third world countries where access to suction generators may not be available.

The aspiration device may also include an integral rapid diagnostic test for analyzing a portion of the aspirated fluid, for example a test strip that detects the presence of Gram-negative bacteria.

FIG. 8 illustrates another embodiment of a handheld aspiration device 800 that can be disposable. The aspiration device 800 comprises a housing or main body 804 that includes an outer surface that provides a handle and is oriented along a central axis 809, a hollow positioning member 807 that extends at least partially along axis 809, a cutting portion or cutting edge 806 located on the distal end of the positioning member, a protective sheath 805 positioned over at least a portion of the positioning member 807, and an actuation member 801 attached to the housing that can reversibly position the sheath 805 such that the cutting portion or edge can be exposed or shielded. As illustrated in FIG. 8, the actuation member 801 is displaced such that sheath 805 exposes the cutting portion 806. Also shown is an attachment hub 803 for attaching a source of negative pressure to allow the device to aspirate fluids, and a weep-hole style actuator 802 to allow the user to direct the negative pressure to the distal end of the positioning member 807 when desired. Any aspirated fluid travels into and is retained in a sterile sample chamber 810 removably attached along a proximal end of housing 804. This chamber can then be swabbed to transfer the sampled fluid to an appropriate transport vial, or the entire chamber can be transported. As illustrated, chamber 810 is located along the same axis (i.e., central axis 809) as is the main body or handle 804 of the aspiration device 800.

FIG. 9A and 9B illustrate yet another embodiment of a handheld aspiration device 900 that can be disposable. Aspiration device 900 comprises a housing or main body 904 that includes an outer surface that provides a handle and is oriented along a central axis 909, a hollow positioning member 907 that extends at least partially along axis 909, a cutting portion or cutting edge 906 located on the distal end of the positioning member, a protective sheath 905 positioned over at least a portion of the positioning member 907, and an actuation member 901 attached to the housing that can reversibly position the sheath such that the cutting portion or edge can be exposed or shielded. In FIG. 9B, the cutting portion or edge 906 is covered by the protective sheath 905. In FIG. 9A, the actuation member 901 is not displaced such that the cutting portion or edge 906 is exposed. Also shown is an attachment hub 903 for attaching a source of negative pressure to allow the device to aspirate fluids, and a weep-hole style actuator 902 to allow the user to direct the negative pressure to the end of the positioning member 907 when desired. Any aspirated fluid travels into and is retained in a sterile sample chamber 910 removably attached along the housing at an orthogonal angle. This chamber can then be swabbed to transfer the sampled fluid to an appropriate transport vial, the entire chamber can be placed in a vial, or the chamber can be capped and used as a transport vial. FIG. 9B shows the internal passageways, highlighting that aspirated fluids can exit the internal passageways or support member inside the sample chamber 910 at location 911.

FIG. 10 illustrates an exploded view of a portion of an aspiration device 1000 under one embodiment. Aspiration device 1000 comprises a main body 1004 that includes an outer surface that provides a handle, a removable nosepiece 1025, a lever actuator 1001 for manipulating the safety sheath that covers and exposes a distal cutting edge on a positioned member (illustrated in FIGS. 2A, 2B, 3A, 3B, 8, 9A and 9B) and a removable sample chamber 1010 for collecting aspirated fluids for microbiological analysis. Internal conduits 1026 for allowing the internal transport of suction and aspirated fluids are illustrated in the exploded view of the handle 1004. A spring 1027 or alternative means of providing a constant force on the actuator 1001 for manipulating the safety sheath ensures that the cutting component (not shown) remains covered only when the user moves the actuator 1001, and that the safety sheath returns to a neutral state where the cutting component is protected when the user removes force from the actuator 1001.

FIG. 11 illustrates another embodiment of a handheld aspiration device 1100 that can be disposable under yet another embodiment. Aspiration device 1100 comprises a housing or main body 1104 that includes an outer surface that provides a handle and is oriented along a central axis 1109, a hollow positioning member 1107 that extends at least partially along axis 1109, a cutting portion or cutting edge 1106 located on the distal end of the positioning member, a sheath positioned over at least a portion of the positioning member 1107, and an actuation member 1101 attached to the housing that can reversibly position the sheath such that the cutting portion or edge can be exposed or shielded. In FIG. 11, the cutting portion or edge 1106 is covered by the protective sheath 1105. Therefore, the actuation member 1101 is not displaced such that the cutting portion 1106 is not exposed. Also shown is an attachment hub 1103 for attaching a source of negative pressure to allow the device to aspirate fluids, and a weep-hole style actuator 1102 to allow the user to direct the negative pressure to the distal end of the positioning member 1107 when desired. Also shown in this embodiment is a mechanical connection component 1113 which interfaces with a mating component on a stabilization system for connecting and registering the components.

In another embodiment, it is possible to physically connect or register a handle of aspiration device with a stabilization system or device. This connection means could consist of a dove-tail type joint with one side of the joint on the handle and the mating side on the stabilization device. A physical locking means, such as a latch or snap could be used to temporarily lock the two components together, or a tapered friction fit could also be used.

FIG. 12 illustrates an alternative embodiment of a mechanical attachment component in the form of one side of a dovetail type joint 1213, which would interface with the mating component found on the stabilization system to register and connect the two components. Alternative means of attachment including a rod and tube, ball and socket, friction fitments, and other mechanical components are also considered. Lower profile embodiments, similar to the dovetailed joint, offer benefits in that if the handheld device is used without a stabilization system, the result is the smallest extension from the device which could impact visualization or other functions.

Figure 13:
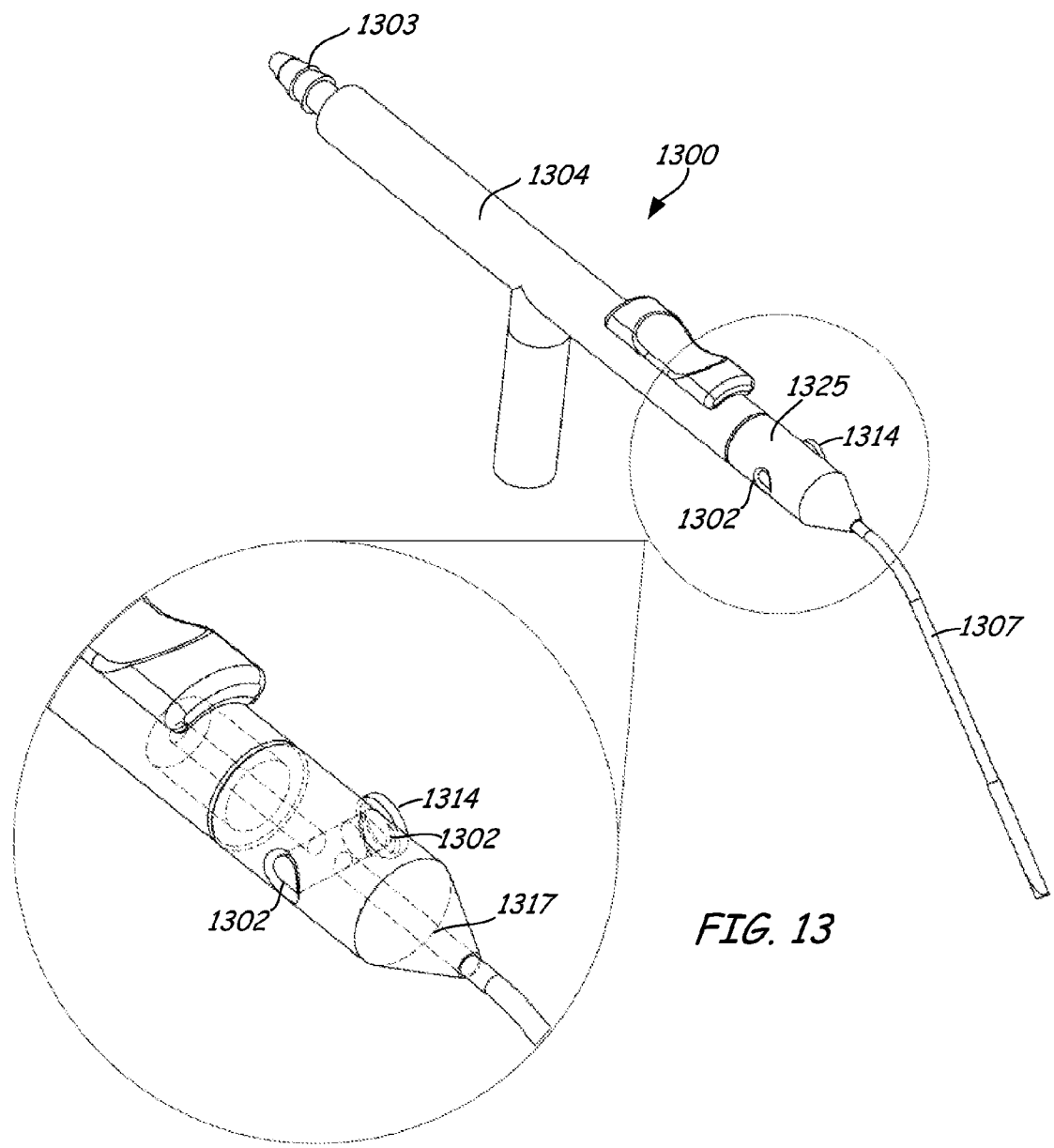
FIG. 13 illustrates an ambidextrous aspiration device having multiple 'weep holes' for actuating suction with a removable plug to block the unused weep hole under yet another embodiment.

FIG. 13 is an enlarged detail view illustrating an embodiment of an aspiration device 1300 with two weep holes 1302 for applying suction to the distal end of the positioning member, and a removable and repositionable plug 1314 which can be positioned in either of the weep holes. This allows the device to be ambidextrous, meaning that the handle or housing and the actuator can be used equally well by a left or right-handed user with respect to suction and actuation. To better achieve this, a nosepiece 1325 may be attached such that it and the positioning member can be positioned independently of the main body, for example by rotating, to allow users to modify the orientation of the device components with respect to one another and to maintain the best sight-lines for how the device is held. In conjunction, positioning member 1307 can be allowed to rotate around the long axis of the handle/housing 1304 to allow further adjustment to enhance the ambidextrous use of the system. Also highlighted in FIG. 13 is a "flash window" 1317 consisting of a clear portion of the device where aspirated fluids can be detected. This allows the user to ensure that a sample has been collected for subsequent microbiological analysis. This or a comparable means of verifying that a fluid sample has been collected ensures that the creation of a myringotomy and fluid collection can be collected in a single pass to minimize patient pain and discomfort. Alternative embodiments to achieving a similar end include a clear or translucent sample chamber, or a clear or translucent placement member.

In one embodiment, the positioning member and protective sheath have a cross-section that is smaller than the cross-section of the body passage or ear canal to be treated such that direct visualization of the membrane to be incised can be visualized alongside the device during insertion. The aspiration device may also include a physical limiter or visual indicator to limit the depth of incision or puncture of the cutting portion. In some cases this may be desirable to reduce the risk of damaging body structures located behind the membrane or tissue being incised, for example the ossicles behind the eardrum. In other cases, it may be desirable to allow the user to pre-select a maximum depth of penetration to allow them to aspirate a sample from a pre-determined location or depth. A physical limiter could be a stop that prevents insertion of the cutting portion beyond a certain point. For example, a physical limiter or stop can be located on the distal end of the protection portion or at a predetermined location on the cutting edge in order to provide a visual or physical indication of a maximum desired depth of penetration during a cutting or puncturing process. In another example, a clinician can use a visual indicator or component as a visible landmark to aid them in determining when an appropriate depth has been reached. In still another embodiment includes a tactile, audible, or visual indication when contact is made with the tympanic membrane and/or when the tympanic membrane is pierced. A resistance measurement means, air pressure measurement means, mechanical force measurement means, or means of measuring any suitable phenomena indicating contact or piercing of a membrane could be used to trigger a tactile feedback mechanism in the handle or stabilization means, generate or alter an audible signal, or generate or alter a visual signal such as an LED light. Measuring a decrease in electrical resistance between the cutting component and an electrically insulated portion of the stabilization system in contact with the patient when the cutting means contacts the membrane would be one embodiment. Using an airflow mass-flowmeter or pressure gauge to detect when the device is in close proximity or piercing the membrane is another embodiment. Force gauges attached to the cutting component, handle, or stabilization means capable of detecting the force created when contacting and/or piercing the membrane is another embodiment. It should be noted that other measurement means for detecting membrane contact and other indicators are considered, and that the preceding examples are not meant to limit the scope of a feedback generating means for detecting membrane contact or puncture.

Figure 14A:
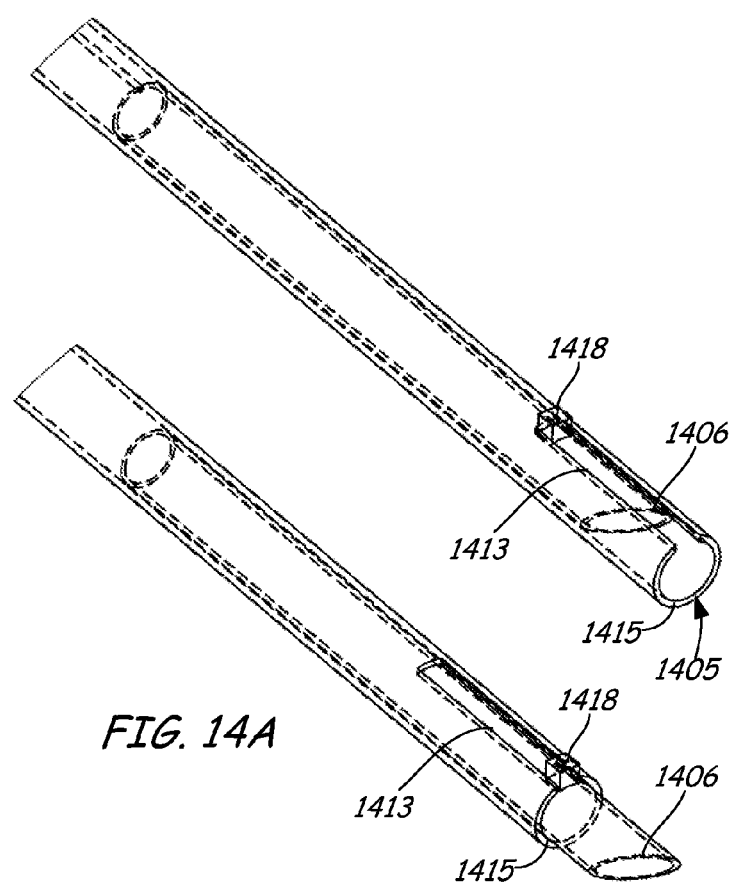
FIGS. 14A and 14B illustrate embodiments of mechanical and visual stops located on the cutting portions and the protective portions of the system.
Figure 14B:
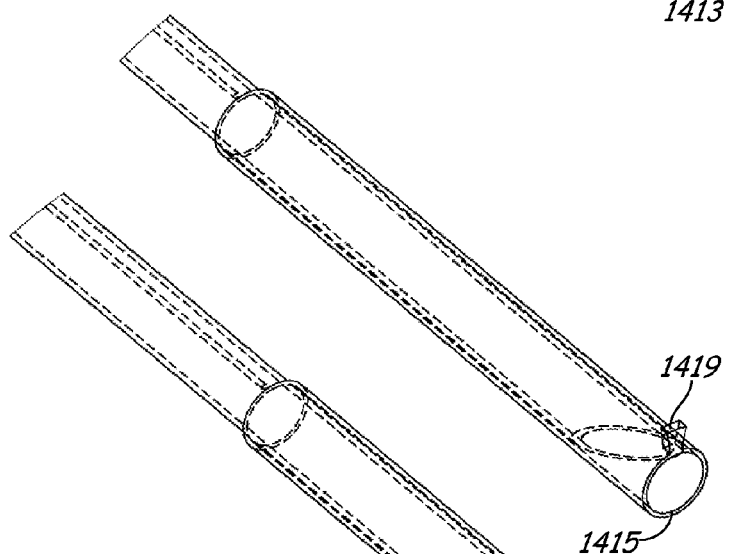

FIG. 14A illustrates an indicator 1418 located on the cutting component 1406 and FIG. 14B illustrates a visual indicator 1419 located on the protective component 1405. These indicators can be used as visual indicators during the procedure to ensure that the cutting edge of the cutting component 1406 is not advanced past the membrane far enough to injure tissue or structures of the middle ear. These indicators could also be used as a secondary physical stop, providing sufficient tactile feedback to allow the user to know when the tympanic membrane has been penetrated. In one example, indicator 1418 is a flange that is oriented perpendicular to the outer surface of the cutting component and located on the cutting component a set distance from the distal end of cutting component 1406 such that it is visible to a user to determine when the cutting component has penetrated sufficiently to pierce the tympanic membrane but is not inserted to a depth where damage to the internal structure of the middle ear will occur. In such an embodiment, protective sheath 1405 includes a slot 1413 that extends from the distal end 1415 of the protective sheath 1405 toward the housing of the aspiration device. The slot 1413 allows the protective sheath 1405 to move along the cutting component 1406 to expose the cutting edge of the cutting component while the user is still able to visualize the indicator 1418. In another example, indicator 1419 is a flange that is oriented perpendicular to the outer surface of the protective sheath 1405 and is located at the distal end 1415. More details regarding a indicator are described in detail in U.S. patent application Ser. No. 12/389,552 published as U.S. 2009/0209972 on Aug. 20, 2009, which is hereby incorporated by reference in its entirety. Such indicators can be included in these and other disclosed embodiments.

Figure 15:
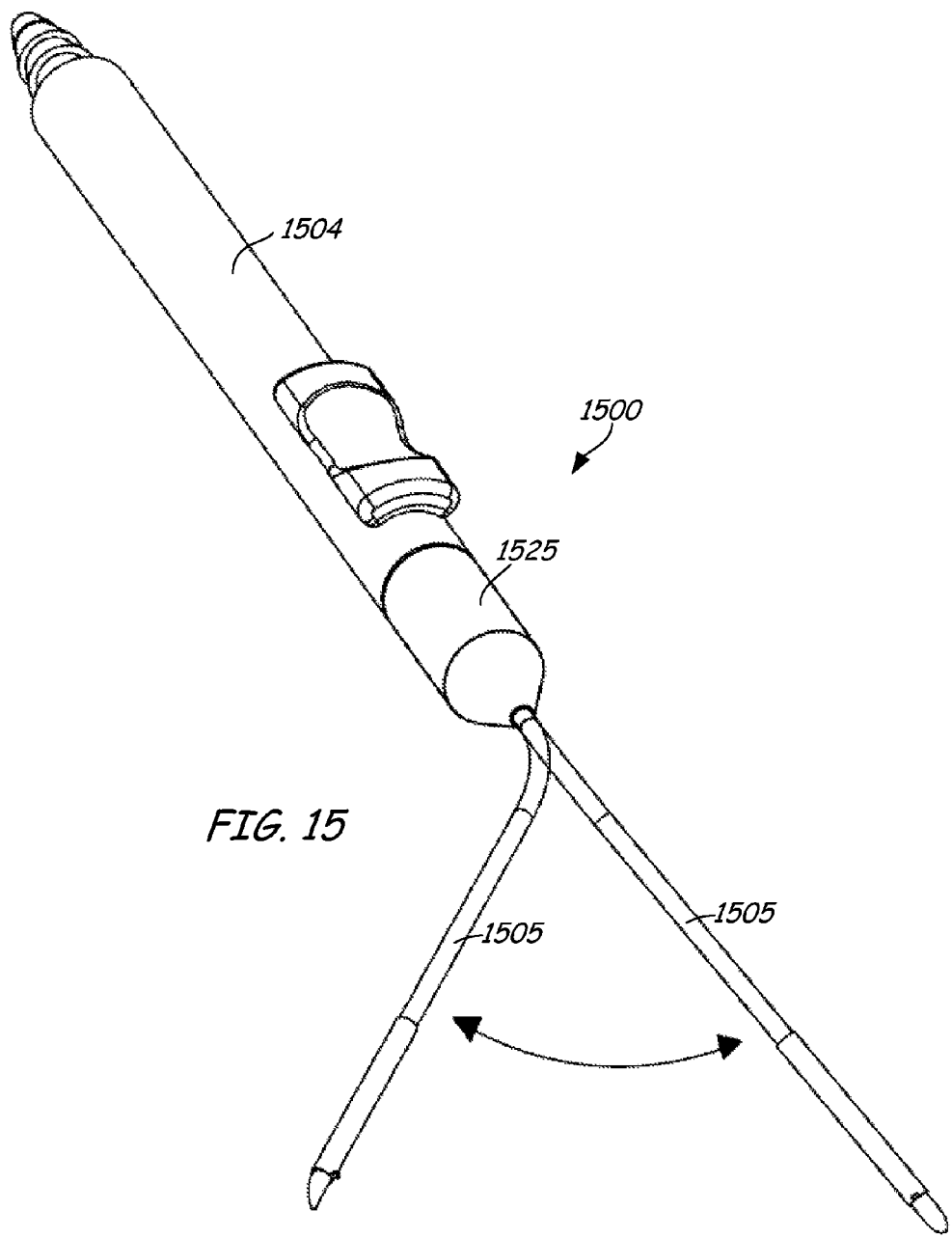
FIG. 15 illustrates an embodiment where the nose tube or the positioning member can be rotated along the long axis of the handle, making it possible for right and left handed users to use a single device.

FIG. 15 illustrates an embodiment of an aspiration device 1500 where the nose tube 1525 or the positioning member 1505 including the cutting edge can be rotated along the long axis of the handle, making it possible for right and left handed users to use a single device. This allows the device to be ambidextrous, meaning that the handle or housing 1504 and the actuator 1501 can be used equally well by a left or right-handed user, with respect to suction and actuation. To better achieve this, a nosepiece 1525 may be attached such that it and the positioning member 1505 can be positioned independently of the main body 1504, for example by rotating as shown in FIG. 15, to allow users to modify the orientation of the device components with respect to one another and to maintain the best sight-lines for how they hold the device. In conjunction, positioning member 1505 can be allowed to rotate around the long axis of the handle/housing 1504 independently of nose piece 1525 to allow further adjustment to enhance the ambidextrous use of the system. In addition, once the rotatable adjustments are made, a locking mechanism, such as a screw, a latch or other alternative element that provides sufficient friction can be used to prevent further relative motion between the main body 1504 and the nose piece 1525 and between the positioning member 1505 and the nose piece 1525 once the desired orientation is achieved. Such a locking mechanism prevents unintended movement or motion during use. Alternatively, a ratcheting mechanism, friction fit or comparable mechanical element that allows adjustability, but prevents the components from moving freely in relation to one another, could be used.

Embodiments of the aspiration device may be used to deploy a shape-memory or super-elastic tympanostomy tube across the tympanic membrane in the myringotomy created. The device could also deploy a simple tube, plug, wick, resorbable implant, or prosthetic across the tympanic membrane in the myringotomy created for purposes including but not limited to ventilation or the application of antibiotics or other medications.

FIGS. 16A-16G illustrate a variety of embodiments of ear tubes or plugs that could be placed using an aspiration device. Round tubes are shown, but other shapes such as flat sections, strings, or alternate geometries that fit within the cutting component could be deployed. More details regarding various embodiments of tubes or tympanostomy tube are described in detail in U.S. patent application Ser. No. 12/389,552 published as U.S. 2009/0209972 on Aug. 20, 2009, which is hereby incorporated by reference in its entirety. Such tubes can be included in these and other disclosed embodiments.

In cases where the device is used to deploy a tube or prosthetic across the tympanic membrane, the actuation mechanism (slide, lever, or the like) used to retract the protective portion to expose the cutting portion could also be used to deploy the tube. A first range of motion of the actuating mechanism could retract the protective portion, and a means of providing tactile feedback could be used to communicate to the user that this first range of motion has been achieved. The cutting portion, with the tube or prosthetic to be deployed located within it, would then be advanced through the tympanic membrane. A second range of motion, either in the same direction or in the opposite direction could then be used to retract the cutting portion, leaving just the tube or prosthetic deployed across the tympanic membrane.

Figure 17:
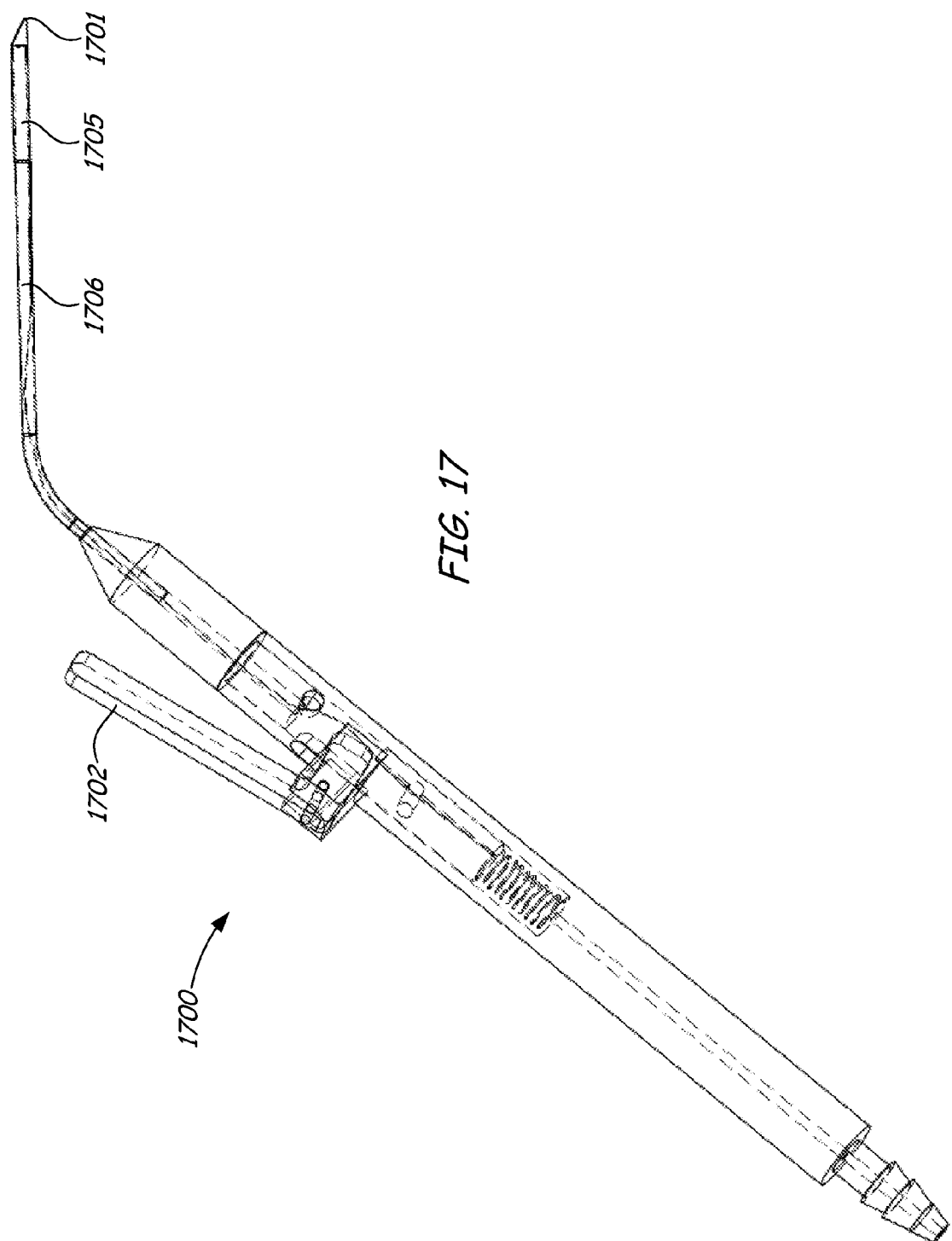
FIG. 17 illustrates an embodiment with an ejection component located inside the cutting component which is capable of displacing an ear tube or prosthetic also located within the cutting component when the cutting and the safety portions are both retracted.

FIG. 17 illustrates one exemplary handheld aspiration device 1700 which has an ejection component 1701 located inside the safety sheath 1705 and the cutting component 1706. This ejection component 1701, or rod, displaces an ear tube or prosthetic from inside the cutting component 1706 when cutting component 1706 is retracted by a secondary or further actuation of the same actuator 1702, or by a secondary actuation means. More details regarding various embodiments of inserting and deploying a tube or tympanostomy tubes are described in detail in U.S. patent application Ser. No. 12/389,552 published as U.S. 2009/0209972 on Aug. 20, 2009, which is hereby incorporated by reference in its entirety. Such details can be included in these and other disclosed embodiments.

FIGS. 18A-18D illustrate a variety of embodiments of cutting component geometries. Shown are simple beveled circular cutting edges 1822, multiple bevel circular cutting edges 1823, a straight cutting edge 1824, and a pointed penetrating tip 1825. Other geometries are also considered. More details regarding various embodiments of cutting edges are described in detail in U.S. patent application Ser. No. 12/389,552 published as U.S. 2009/0209972 on Aug. 20, 2009, which is hereby incorporated by reference in its entirety. Such edges and geometries can be included in these and other disclosed embodiments.

FIGS. 19A and 19B illustrate additional embodiments of handheld aspiration devices 1900A and 1900B that can be disposable. In FIG. 19A, aspiration device 1900A is an exploded view and in FIG. 19B, the aspiration device 1900B is assembled. Aspiration devices 1900A and 1900B comprise a housing or handle 1904, a hollow positioning member or member 1907, an attachment hub 1903 for receiving a source of negative pressure to allow the device to aspirate fluids, a weep-hole style actuator 1902, and an actuation member 1901 attached to the housing that can reversibly position a protective sheath 1905 such that the cutting portion can be exposed or shielded. Housing 1904 can include internal volumes for the collection of fluids aspirated. For example, these volumes could be an integral part of housing 1904, or could be removable, such as by screw fitting or luer lock, for subsequent transportation to an appropriate laboratory setting for microbiological analysis. The device may include a sterile sample collection component that allows aspirated fluids to be transported. While the fluids may be directly aspirated into this collection component, the device may also have a portion of the aspiration conduit that is removable, for example a section of the positioning member or nosepiece that can be removed and placed into a sterile sample vial for transport to a lab. For example, the housing could have an integral, removable swab in an internal volume that is exposed to aspirated fluids. This swab could then be used for testing purposes. Additionally, the housing that contains the swab could be entirely removable, creating a transport mechanism for getting the aspirated sample to the lab on a swab that can be used for culture purposes. In another example, the housing could have a removable sterile vial as part of the housing, and the removable portion of the fluid conduit that retains sufficient aspirate for testing could be removed, or 'snapped off' and placed into said vial for transport. This provides an economic benefit to the caregiver by providing all of the sterile components necessary to acquire, store, and transport, aspirated samples for subsequent microbiologic analysis.

As illustrated in FIG. 19A, a removable nosepiece 1925 is in axial alignment with housing 1904 and is configured to engage with housing 1904 at one end and configured to couple to positioning member 1907 at an opposing end. In FIG. 19A, nosepiece 1925 can contain a chamber for collecting fluids sampled during aspiration, and can be removed for swabbing or removed for transport. In addition, a break-off portion or cutting component 1907B having cutting edge 1906 can be assembled to positioning member 1907. Cutting component 1907B would also contain traces of any aspirated fluid and could be placed into a sterile vial for subsequent microbiological analysis. As illustrated in FIG. 19B, rather than nosepiece 1925 being removable and containing a chamber for collecting fluids sampled during aspiration, a chamber 1910 for collecting fluids sampled during aspiration can engage with and be located orthogonally to housing 1904. Chamber 1910, shown in its detached state, can be removed for swabbing or used for transport. It should be realized that a swab or suitable absorbent means 1931 located in the sampling chamber 1910 or in nosepiece 1925, which would contain traces of any aspirated fluid could be placed into a sterile vial for subsequent microbiological analysis, or used to transport sampled fluid from the sampling chamber to an appropriate storage vial.

The aspiration device may comprise a housing capable of holding a sterile sample vial under negative pressure, for example a Vacutainer tube (BD, Franklin Lakes, N.J.), which may also contain culture media. The actuation of the suction function by the user would result in the proximal end of the positioning member piercing the friable cap of the vacutainer, such that the negative pressure in the tube would create the necessary suction to aspirate fluids into the tube. The tube could then be detached from the housing and used to transport the samples to a laboratory for testing purposes.

In FIG. 19A, the positioning member 1907, the cutting component 1907B and the protective sheath 1905 can all be preassembled to removable nosepiece 1925 to form a nosepiece assembly. In such a design, it would be possible to provide multiple sizes and/or geometries of the preassembled piece such that a clinician could choose the best option for the task at hand. In the alternative, positioning member 1907, cutting component 1907B, the protective sheath 1905 and nose piece 1925 can be separately presented for assembly by the clinician such that the clinician could choose the best option for each individual component for the task at hand. For example, a larger cutting portion on a longer, thicker positioning member may be suitable for creating a myringotomy in an adult, while a smaller cutting portion and a shorter, thinner positioning member may be required to accomplish the same task on a very young child.

In one embodiment, the housing 1904 or nosepiece 1925 of the device contains an energy source, such as a battery, capable of powering a light emitting diode or equivalent light source, for the purpose of providing additional light along the positioning member. This light could be located on the handle or at any point along the positioning member and/or safety portion. The light could also be in communication with a means of funneling the light alongside the positioning member, such as a fiber optic filament, thereby allowing the light to be directed further along the positioning member without moving the bulk of the light source out along the positioning member, which could impact sight lines or the ability of the member to be inserted into confined anatomical spaces or passages.

Figure 20:
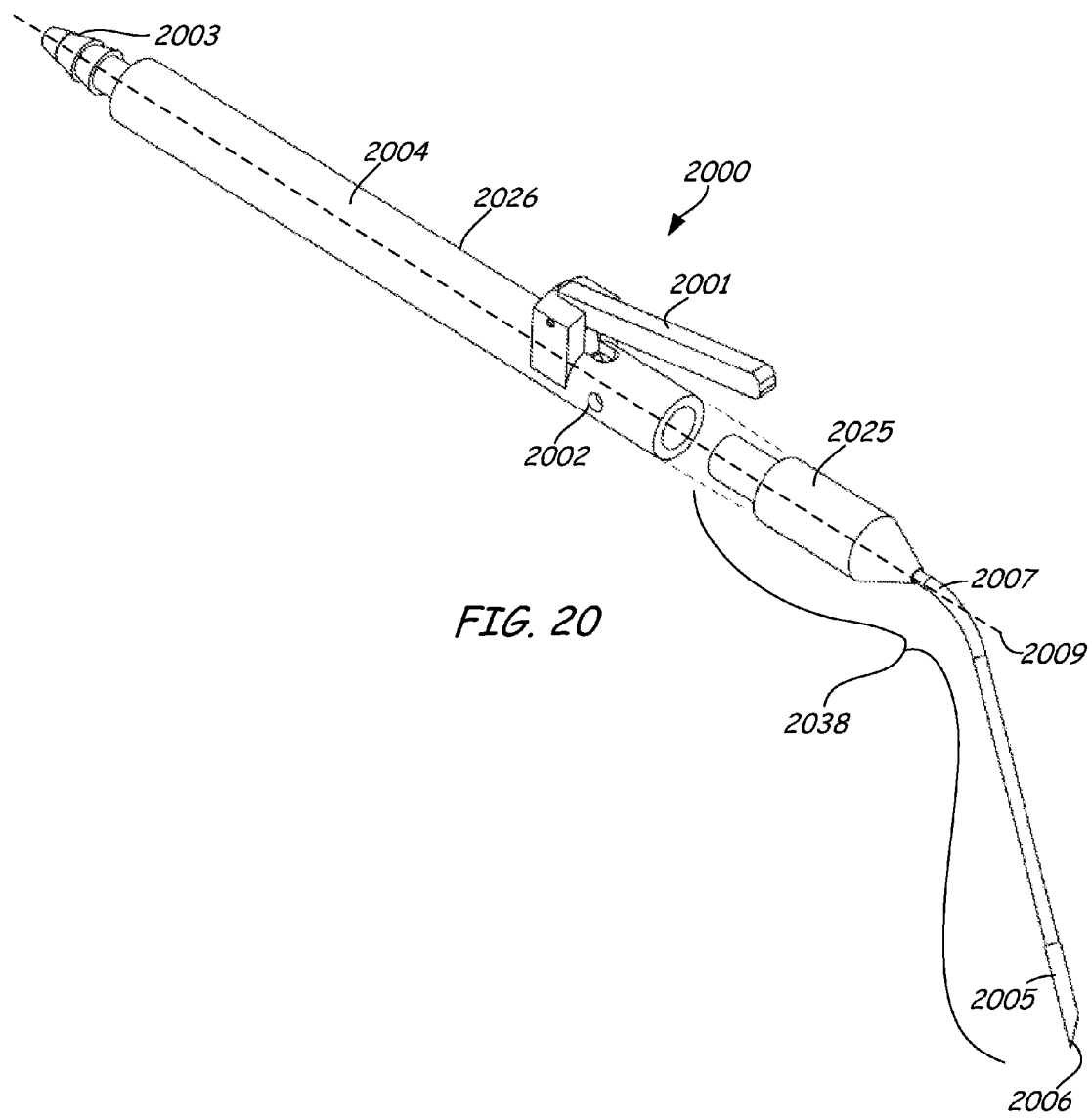
FIG. 20 illustrates an embodiment where the cutting and safety portions of the device can be removed from the handle and actuation portion of the device, allowing the user to interchange components to achieve a desired size or place multiple ear tubes with a single handle component.

FIG. 20 illustrates another embodiment of a handheld aspiration device 2000 that can be disposable. Aspiration device 2000 comprises a housing or main body 2004 that includes an outer surface that provides a handle and is oriented along a central axis 2009, a hollow positioning member 2007 that extends at least partially along axis 2009, a cutting component or cutting edge 2006 located on the distal end of the positioning member, a protective sheath 2005 positioned over at least a portion of the positioning member 2007, and an actuation member 2001 attached to the housing that can reversibly position the sheath such that the cutting portion can be exposed or shielded. The cutting edge 2006 is configured to be covered by the protective sheath 2005. When the actuation member 2001 is displaced, the cutting portion 2006 is exposed. Also shown is an attachment hub 2003 for attaching a source of negative pressure to allow the device to aspirate fluids, and a weep-hole style actuator 2002 to allow the user to direct the negative pressure to the end of the positioning member 2007 when desired.

As illustrated in FIG. 20, housing 2004 can be constructed from multiple components, including a main body 2026 and a removable/replaceable nosepiece 2025. These components are capable of being assembled by the user. In one embodiment, the nosepiece 2025 can contain the cutting portion and the components necessary for actuating the sheath, and the main body 2026 can contain the actuation mechanism 2001, or trigger, that the user manipulates to change the position of the protective sheath 2005, thereby exposing or protecting the cutting portion of the device. When the main body 2026 and the nosepiece 2025 are assembled, such as by a snap fit or a friction fit, the trigger mechanism 2001 in the body interfaces with the sheath actuation components in the nosepiece 2025 as necessary to provide the required movement of the protective sheath 2005 in response to user manipulation of the actuation component 2001. In one embodiment, a source of negative pressure passes through the main body from attachment hub 2003. In this embodiment, connecting conduits between the main body 2026 and the nosepiece 2025 transmits negative pressure from the main body 2026 to the nosepiece 2025. The housing 2004 as described would allow the end user to select from multiple different types and sizes of positioning members and therefore cutting components and an internal volume for collecting aspirated fluids could be incorporated into the nosepiece 2025, which would allow a user to obtain and segregate multiple samples for diagnostic purposes using a single main body 2026.

As illustrated in FIG. 20, it can be seen that the nosepiece 2025 of the device along with the protective sheath 2005 and positioning member 2007 are removable from the device and can be interchangeable between varieties of different sizes. In this way, a user could choose from a number of different diameters of cutting portion, lengths of positioning members, or type of ear tube or prosthetic to be implanted (in the case of a device configured to al implant an ear tube) by simply attaching the correct nosepiece assembly 2038 to the device. It should be noted that the suction actuator 2002 is shown on the housing or handle in this embodiment, but could also be located on the removable section or removable nosepiece assembly 2038.

Figure 21:
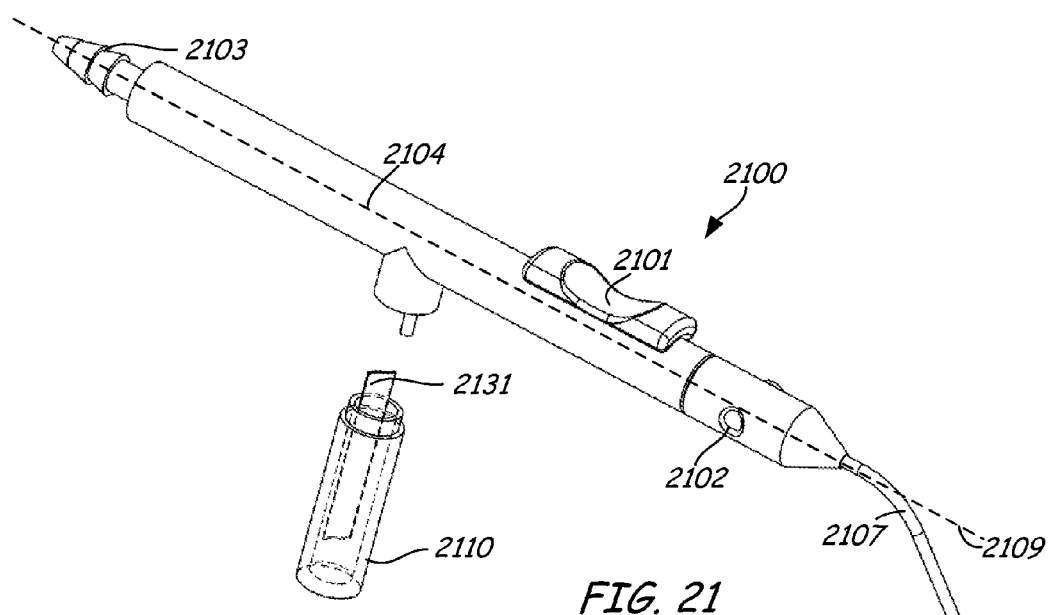
FIG. 21 illustrates an embodiment with a rapid diagnostic test strip located in the sampling chamber to allow for an immediate microbiologic assessment of sampled fluids.

FIG. 21 illustrates an alternate embodiment of a disposable handheld aspiration device 2100 comprising a housing or main body 2104 that includes an outer surface that provides a handle and is oriented along a central axis 2109, a hollow positioning member 2107 that extends at least partially along axis 2109, an attachment hub 2103 for attaching to or receiving a source of negative pressure to allow the device to aspirate fluids, a weep-hole style actuator 2102, and an actuation member 2101 attached to the housing 2104 that can reversibly position a protective sheath 2105 such that a cutting portion located on the distal end of the positioning member 2107 can be exposed or shielded. The device 2100 also includes a chamber 2110 for collecting fluids sampled during aspiration, which can be removed for swabbing or used for transport, is shown in its detached state. An integral rapid diagnostic test 2131 for analyzing a portion of the aspirated fluid, for example a test strip that detects the presence of Gram-negative bacteria, is located in the sampling chamber 2110 where it would be exposed to any aspirated fluid. At least a portion of the fluid being aspirated is drawn into a portion of the housing where it can be combined with the appropriate reagents and indicators to provide a visible indication of the nature of the bacteria, if present, in the sample. Reagents could be present in the portion of the housing used for the diagnostic test, added via a port or syringe by the caregiver at the appropriate time, or brought into contact with aspirated fluids by breaking a friable barrier between the reagents and the sample. Therefore, the rapid diagnostic test could provide a visual indication of the test outcome in-situ in the sample chamber via a visual indicator, such as a color change, or could be removed from the sample chamber and exposed to further analysis.

Figure 22:
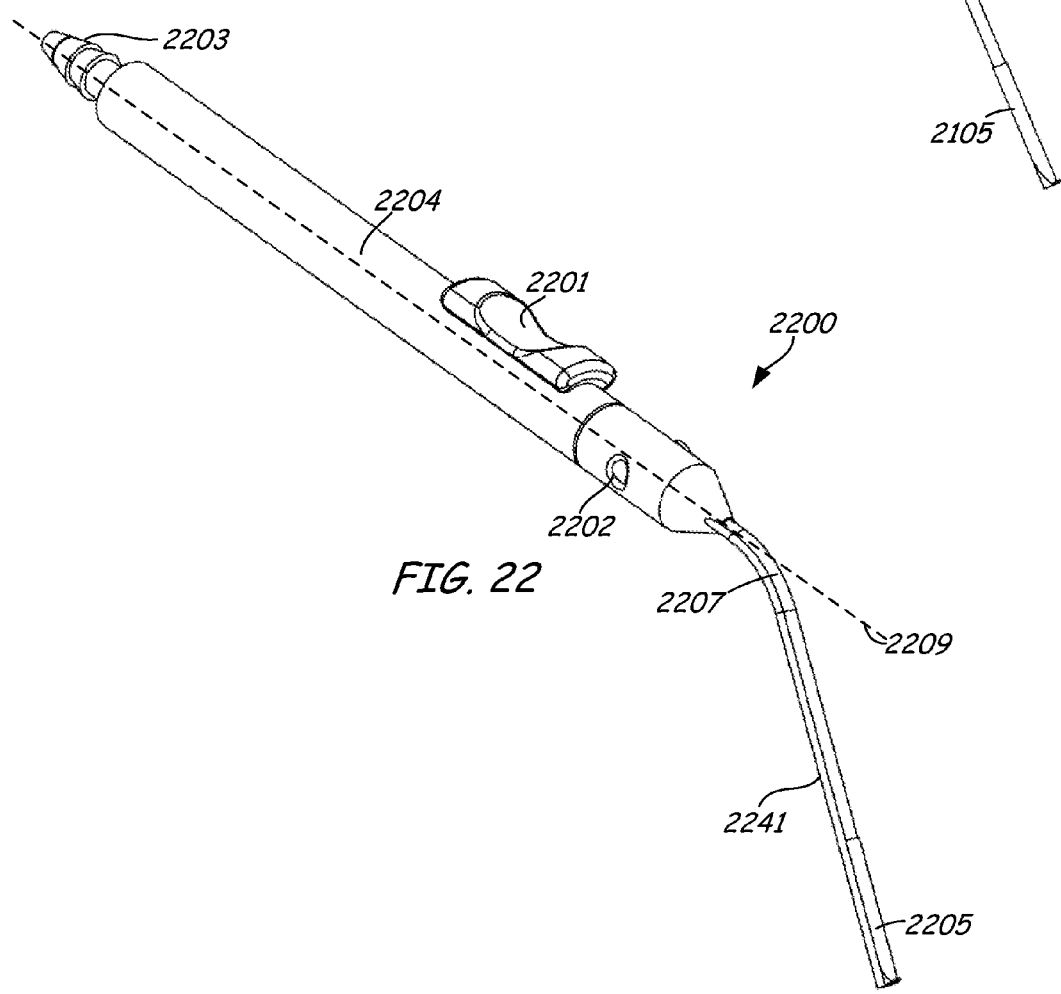
FIG. 22 illustrates an embodiment with a secondary channel extending along the length of the positioning member to allow the deliver of drugs or analgesics to the ear canal or to the middle ear.

FIG. 22 illustrates an alternate embodiment of a handheld aspiration device 2200 that can be disposable. Aspiration device 2200 includes a housing or main body 2204 that includes an outer surface that provides a handle and is oriented along a central axis 2209, a hollow positioning member 2207 that extends at least partially along axis 2209, an attachment hub 2203 for attaching or receiving a source of negative pressure to allow the device to aspirate fluids, a weep-hole style actuator 2202, and an actuation member 2201 attached to the housing that can reversibly position the sheath such that the cutting portion can be exposed or shielded. Aspiration device 2200 has the ability to inject medication, for example a local anesthetic or a local antibiotic, at one or more points along the positioning member. For injecting a local anesthetic, it may be desirable to inject from the distal end of the device and at one or more locations along the positioning member in close proximity to the distal end. For injecting an antibiotic, it may be desirable to inject from the distal end, for example to allow an antibiotic to be deposited in the middle ear to treat an infection. For example and as illustrated in FIG. 22, running along the length of positioning member 2207 is another conduit or passage 2241 that can be used to apply drugs, analgesics, or other medications along the ear canal, to the tympanic membrane, or to the middle ear. While the conduit shown is a tube running parallel to the positioning member 2207, it should be realized that a conduit located concentric with or internal to positioning member 2207 is also considered. Also, while a single conduit is shown, multiple conduits of the same or different lengths could be used. Conduits could have an outlet at the end, as illustrated, or an outlet or multiple outlets located along their length in addition to or in place of an outlet at the far end.

Figure 23:
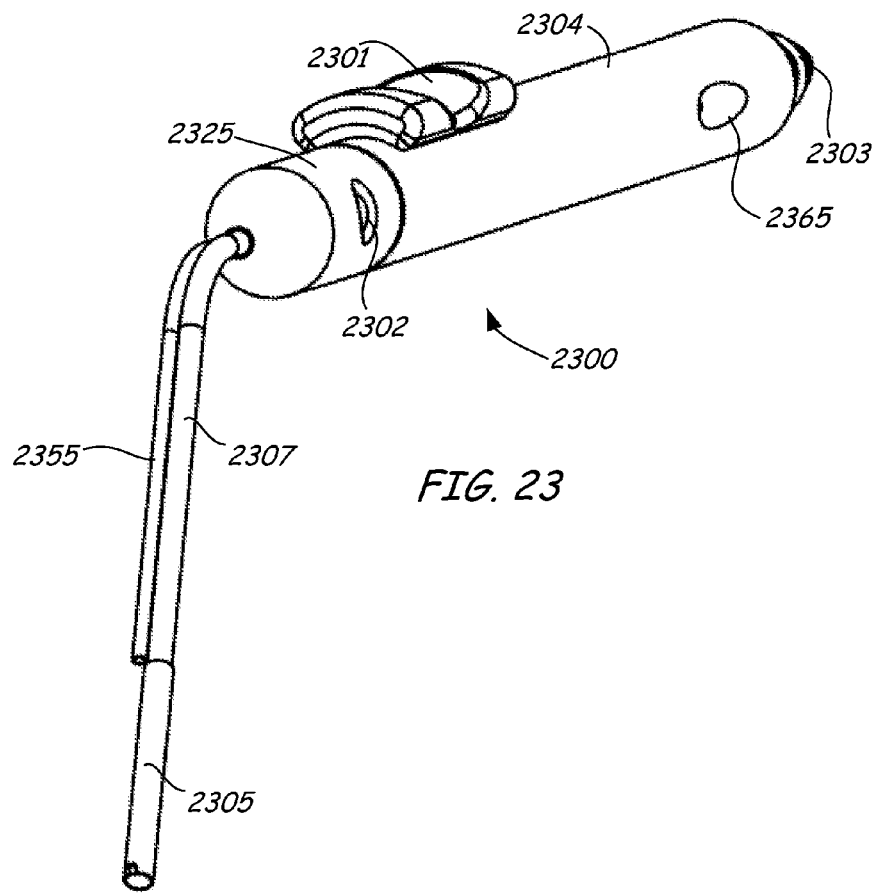
FIG. 23 illustrates an embodiment with a fiber optic imaging device extending along a portion of the length of the positioning member to allow improved visualization of the cutting portion of the device even when the end is penetrating the tympanic membrane.

FIG. 23 illustrates an alternative embodiment of a handheld aspiration device 2300 comprising a housing or handle 2304, a hollow positioning member 2307, an attachment hub 2303 for attaching or receiving a source of negative pressure to allow the device to aspirate fluids, a weep-hole style actuator 2302, and an actuation member 2301 attached to the housing that can reversibly position the sheath such that the cutting portion can be exposed or shielded. A fiber optic scope 2355 is shown positioned alongside the positioning member 2307 such that the cutting portion of the device and the tympanic membrane could be clearly visualized even while the cutting portion of the device is located behind the tympanic membrane. While the fiber optic scope could be positioned at the end of the positioning member, visibility would be impaired or eliminated by having the imaging device too close to the membrane to focus or see a sufficiently large enough field of view. While the imaging system could be integral with the handle 2304, it is also possible that an internal passage with an opening on the handle 2365 could allow the passage of existing fiber optic components through the handle and into position inside the positioning member 2307 or alongside the positioning member 2355.

Embodiments of the aspiration device can also include a delivery means capable of administering local anesthetics, vascocontrictors, or analgesics, such as lidocaine, bupivacaine, tetracaine, ropivacaine, chloroprocaine, and phenol, to the ear canal and/or the tympanic membrane. These could be distributed via the same passage used for aspirating fluids, or a secondary passage could be employed. The use of multiple, small exit orifices to assist in atomizing or equally distributing the anesthetics or analgesics is also considered.

Figure 24:
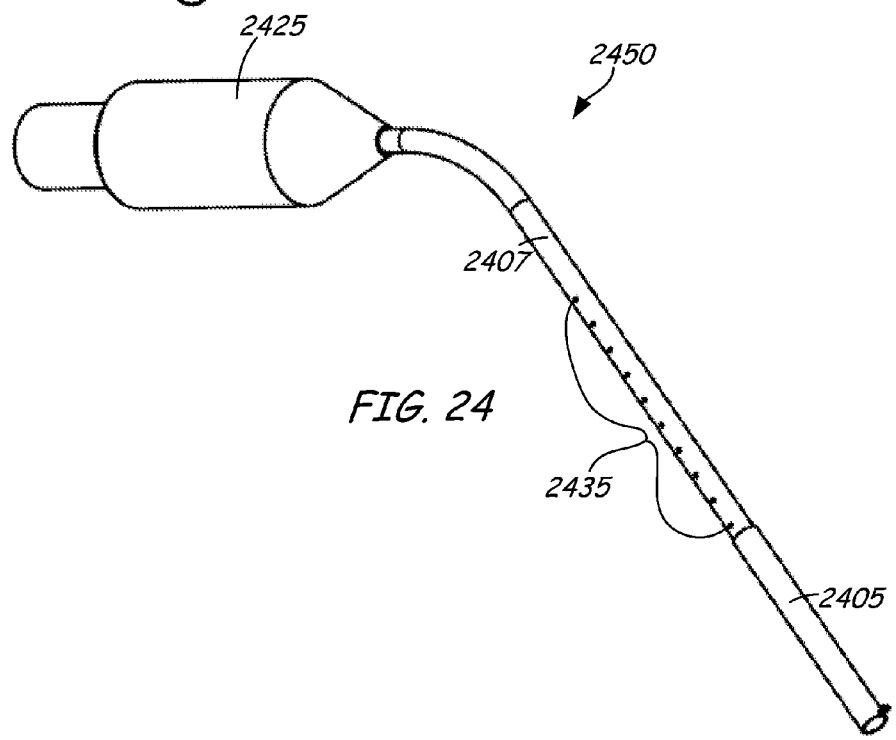
FIG. 24 illustrates an alternative embodiment of the positioning member which has a multitude of openings along the length of the positioning member to allow for the delivery of drugs such as analgesics and anesthetics.

FIG. 24 illustrates an embodiment of a drug delivery element 2450 of a disposable handheld aspiration device. Shown are a plurality of small holes 2435 located along the length of a positioning member 2407. Also shown is a protective sheath 2405 and a nosepiece 2425 which could connect to the main body and remaining elements of the aspiration device. The aspiration device has the ability to inject medication, for example a local anesthetic or a local antibiotic, from the plurality of holes located along the positioning member.

It should be realized that a stabilization system or device can perform many of the functions required by described embodiments of the aspiration device that don't require sterile and/or clean components. For example, the protective sheath actuation means and/or the suction actuation means could be re-usably incorporated into the stabilizer, with the sterile components such as the sampling chamber, cutting components, protective sheath, and positioning member disposably attaching to the stabilizer. The connections could be a friction fit type, luer-type, screw type, or other suitable design. Keeping as many of the systems functions associated with the re-usable stabilizer component would minimize waste and cost, and potentially maximize flexibility for the end user by allowing them to mix and match from a range of attachable components, such as cutting edges, sampling vials, negative pressure means, and ear tubes or prosthetics.

It should be noted that the means of limiting the axial movement of the cutting edge toward the patient may be enabled by the stabilization means, but the actual degree of travel allowed could be determined and controlled by the handle or main body of the aspiration device. For example, upon locking the stabilization system in place, correct positioning of the handle or main boy is achieved. In addition, the actuating mechanism on the handle could extend the cutting portion a pre-determined distance instead of retracting the sheath.

Figure 25A:
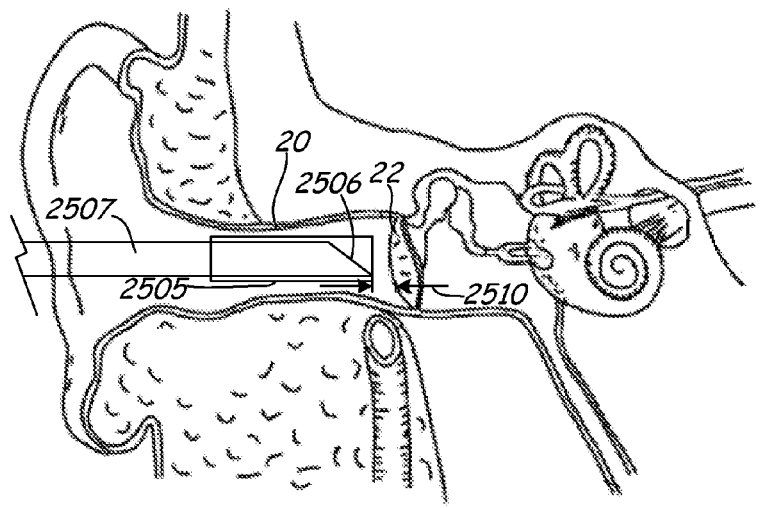
FIGS. 25A-25E illustrate diagrammatic views of performing a myringotomy with an aspiration device in accordance with one embodiment.
Figure 25B:
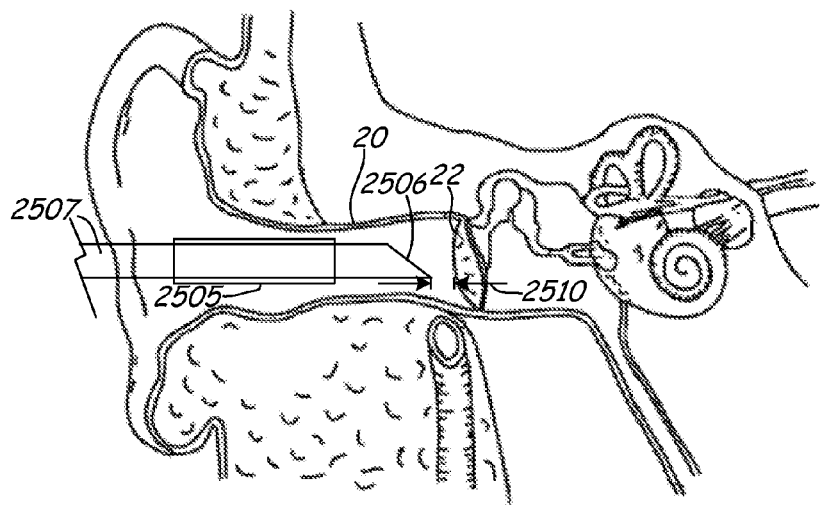

FIGS. 25A-25E illustrate diagrammatic views of performing a myringotomy in accordance with one embodiment. In FIG. 25A, together at least portions of hollow positioning member 2507 including cutting edge 2506 and protective sheath 2505 are manually inserted into an ear canal 20 of a patient using an outer surface of the main body as a handle. The positioning member 2507, the protective sheath 2505 and the cutting edge 2506 are advanced together such that the cutting edge 2506 and the protective sheath 2505 are located a spaced distance 2510 from the tympanic membrane 22. In this position, the protective sheath 2505 covers the cutting edge 2506 and is a first position of the moveable protective sheath. As illustrated in FIG. 25B, the protective sheath 2505 is actuated while the positioning member 2507 and the cutting edge 2506 remain in place such that the protective sheath 2505 slides relative to and along the positioning member to expose the cutting edge 2506. In this position, the protective sheath 2505 is in a second position. In some embodiments, protective sheath 2505 can slide over positioning member 2507 along the same axis as the central axis of the main body of the device. In other embodiments, however, protective sheath 2505 is slid over positioning member 2507 along an axis that is orthogonal to the axis at which the main body is located.

Figure 25C:
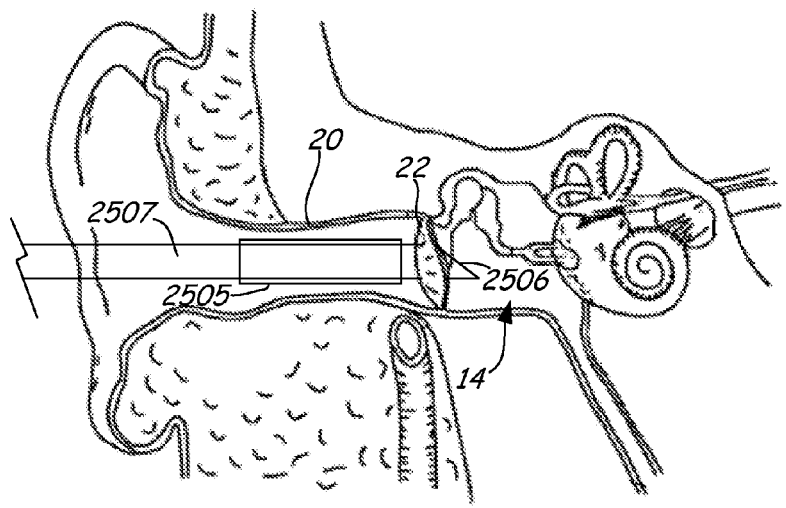
Figure 25D:
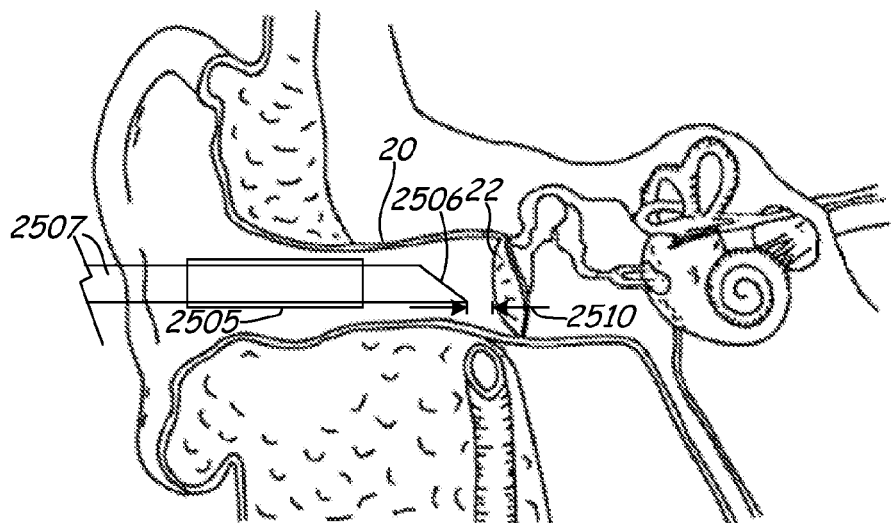
Figure 25E:
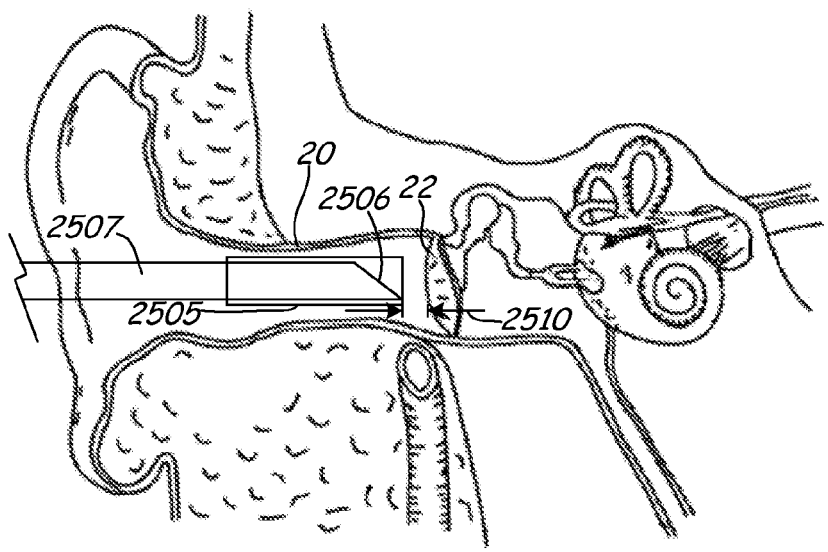

In FIG. 25C, the positioning member 2507, the cutting edge 2506 and the actuated protective sheath 2505, which is in the second position, are manually advanced using the handle of the device such that the cutting edge 2506 pierces the tympanic membrane 22 to form the myringotomy. In FIG. 25D, the positioning member 2507, the cutting edge 2506 and the actuated protective sheath 2505, which is still in the second position, are manually retracted back into the ear canal 20 such that the cutting edge 2506 is again located the spaced distance 2510 from the tympanic membrane 22. In FIG. 25E, protective sheath 2505 is actuated while the positioning member 2507 and the cutting edge 2506 remain in place such that the protective sheath 2505 slides relative to and along the positioning member 2507 to again cover the cutting edge 2506. In this position, the protective sheath 2505 returns to the first position. Before the positioning member 2507, the cutting edge 2506 and the protective sheath 2505 are manually extracted or removed from the ear canal 20 using the handle, suction can be applied to the most distal end of the device (i.e., the distal end of positioning member 2507, cutting edge 2506 or protective sheath 2505) to aspirate fluid that is draining from middle ear 14.

Although embodiments have been described with reference to preferred embodiments, workers skilled in the art will recognize that changes may be made in form and detail without departing from the spirit and scope of the invention.

What is claimed is:

1. A device for performing a myringotomy, the device comprising:
   a main body oriented along a central axis having a proximal end, a distal end and an outer surface, the main body including an attachment hub for receiving components that provide suction;
   a hollow positioning member coupled to the main body and including a distal end, the positioning member extending at least partially along the central axis;
   a cutting edge for piercing a tympanic membrane of a body;
   a protective sheath; and
   an actuator located on the main body, the actuator configured to move the protective sheath from a first position that surrounds the cutting edge to a second position that exposes the cutting edge and from the second position back to the first position.

2. The device of claim 1, wherein the cutting edge is located on the distal end of the positioning member.

3. The device of claim 2, further comprising a visual indicator for indicating a maximum depth of penetration of the cutting edge when the cutting edge is exposed.

4. The device of claim 3, wherein the visual indicator comprises a flange coupled to and extending outwardly from a distal end of the protective sheath.

5. The device of claim 3, wherein the visual indicator comprises a flange coupled to and extending outwardly from the positioning member at a location proximal to and a spaced distance from the cutting edge.

6. The device of claim 2, further comprising a removable nosepiece coupled to the distal end of the main body, the removable nosepiece configured to retain a proximal end of the positioning member.

7. The device of claim 1, wherein the main body further comprises a removable chamber for collecting fluids draining through the myringotomy using the components that provide suction.

8. The device of claim 1, wherein the actuator is a slider-type component that protrudes from the outer surface of the main body and is moveable along an axis that is parallel with the central axis.

9. A method of performing a myringotomy comprising:
   obtaining a device including a main body, a hollow positioning member, a cutting edge and a protective sheath, wherein the positioning member, the cutting edge and the protective sheath are located distal to the main body;
   manually inserting at least portions of the positioning member, the cutting edge and the protective sheath into an ear canal of a patient using an outer surface of the main body as a handle, wherein the positioning member, the protective sheath and the cutting edge are advanced together such that the cutting edge and the protective sheath are located a spaced distance from the tympanic membrane and wherein the protective sheath covers the cutting edge;
   actuating the protective sheath while the positioning member and the cutting edge remain in place such that the protective sheath slides relative to and along the positioning member to expose the cutting edge;
   manually advancing the positioning member, the cutting edge and the actuated protective sheath using the handle such that the cutting edge pierces the tympanic membrane;
   manually retracting the positioning member, the cutting edge and the actuated protective sheath such that the cutting edge is again located the spaced distance from the tympanic membrane;
   actuating the protective sheath while the positioning member and the cutting edge remain in place such that the protective sheath slides relative to and along the positioning member to again cover the cutting edge; and
   manually extracting the positioning member, the cutting edge and the protective sheath from the ear canal using the handle.

10. The method of claim 9, wherein the cutting edge is located on the distal end of the positioning member.

11. The method of claim 10, further comprising using a visual indicator located on one of the positioning member or the protective sheath for indicating a maximum depth of penetration of the cutting edge when the cutting edge is exposed.

12. The method of claim 9, further comprising applying suction after the cutting edge is retracted from the tympanic membrane to aspirate fluid being drained through the myringotomy.

13. The method of claim 12, further comprising collecting the aspirated fluid in a removable chamber that is removably coupled to the main body of the device.

14. The method of claim 9, wherein obtaining a device comprises:
   obtaining the main body that extends along an axis and has a proximal end, a distal end and an outer surface; and
   selectively obtaining a removable assembly removably coupled to the distal end of the main body, the removable assembly including a nosepiece that is removably coupled to the distal end of the main body, the hollow positioning member, the cutting edge and the protective sheath;
   wherein the removable assembly is selectively obtained from a plurality of differently sized removable assemblies based on anatomy specific to a patient for whom the myringotomy is to be performed on.

15. The method of claim 9, further comprising means for deploying a tympanostomy tube in the myringotomy after the cutting edge pierces the tympanic membrane.

16. A device for performing a myringotomy, the device comprising:
   a main body extending along a central axis having a proximal end, a distal end and an outer surface that provides a handle, the main body including an attachment hub for receiving components that provide suction;
   a rotatable assembly coupled to the distal end of the main body, the rotatable assembly comprising:
      a nosepiece rotatably coupled to the cylindrical main body and extending along the central axis;
      a hollow positioning member fixed to the nosepiece, the positioning member extending at least partially along the axis and partially along an axis orthogonal to the central axis;
      a cutting edge being capable of piercing a tympanic membrane of a body; and
      a protective sheath slidable along the positioning member between a first position and a second position, wherein in the first position the protective sheath covers the cutting edge and in the second position the protective sheath exposes the cutting edge;
      wherein the rotatable nosepiece is adjustable such that the hollow positioning member can be oriented in more than one direction relative to the central axis.

17. The device of claim 16, wherein the cutting edge is located on a distal end of the positioning member.

18. The device of claim 16, further comprising a cutting component removably coupled to a distal end of the positioning member and including the cutting edge.

19. The device of claim 16, further comprising a visual indicator for indicating a maximum depth of penetration of the cutting edge when the cutting edge is exposed, wherein the visual indicator comprises a flange coupled to and extending outwardly from a distal end of the protective sheath.

20. The device of claim 16, further comprising a visual indicator for indicating a maximum depth of penetration of the cutting edge when the cutting edge is exposed, wherein the visual indicator comprises a flange coupled to and extending outwardly from the positioning member at a location proximal to and a spaced distance from the cutting edge.

* * * * *